(12) United States Patent
Burton et al.

(10) Patent No.: US 11,690,704 B2
(45) Date of Patent: *Jul. 4, 2023

(54) METHOD AND APPARATUS FOR MONITORING IMPLANTABLE DEVICE FOR URINARY CONTINENCE

(71) Applicant: Uromedica, Inc., Plymouth, MN (US)

(72) Inventors: John H. Burton, Minnetonka, MN (US); Timothy C. Cook, Wayzata, MN (US)

(73) Assignee: Uromedica, Inc., Plymouth, MN (US)

( * ) Notice: Subject to any disclaimer, the term of this patent is extended or adjusted under 35 U.S.C. 154(b) by 78 days.

This patent is subject to a terminal disclaimer.

(21) Appl. No.: 17/302,531

(22) Filed: May 5, 2021

(65) Prior Publication Data
US 2021/0251737 A1   Aug. 19, 2021

Related U.S. Application Data

(63) Continuation of application No. 16/450,246, filed on Jun. 24, 2019, now Pat. No. 11,510,766.
(Continued)

(51) Int. Cl.
*A61F 2/00* (2006.01)
*A61B 17/00* (2006.01)
*A61F 2/04* (2013.01)

(52) U.S. Cl.
CPC ............. *A61F 2/004* (2013.01); *A61F 2/04* (2013.01); *A61B 2017/00805* (2013.01); *A61F 2/0045* (2013.01); *A61F 2002/047* (2013.01)

(58) Field of Classification Search
CPC .......................................... A61B 2017/320048
(Continued)

(56) References Cited

U.S. PATENT DOCUMENTS 2,687,131 A   8/1954   Raiche
3,138,161 A   6/1964   Allen
(Continued)

FOREIGN PATENT DOCUMENTS

CA   2022709   2/1991
CN   113677295   11/2021
(Continued)

OTHER PUBLICATIONS

U.S. Appl. No. 17/302,529, filed May 5, 2021, Method and Apparatus for Monitoring Implantable Device for Urinary Continence.
(Continued)

*Primary Examiner* — Kaylee R Wilson
(74) *Attorney, Agent, or Firm* — Schwegman Lundberg & Woessner, P.A.

(57) ABSTRACT

One or more sensors are incorporated onto one or more of an implantable device and a surgical tool used for placement and/or adjustment of the implantable device. The implantable device includes an adjustable membrane element for controllable coaptation of a body lumen, such as coaptation of a urethra as treatment for urinary incontinence. In various embodiments, the one or more sensors can be configured to detect information indicative of at least one of a shape of the adjustable membrane element, a position of the adjustable membrane element relative to the body lumen, or a shape of the body lumen.

20 Claims, 15 Drawing Sheets

Related U.S. Application Data

(60) Provisional application No. 62/805,503, filed on Feb. 14, 2019.

(58) Field of Classification Search
USPC .......................................................... 600/207
See application file for complete search history.

(56) References Cited

U.S. PATENT DOCUMENTS

| | | | |
|---|---|---|---|
| 4,019,499 A | 4/1977 | Fitzgerald |
| 4,428,365 A | 1/1984 | Hakky |
| 4,545,367 A | 10/1985 | Tucci |
| 4,553,959 A | 11/1985 | Hickey et al. |
| 4,559,043 A | 12/1985 | Whitehouse et al. |
| 4,592,339 A | 6/1986 | Kuzmak et al. |
| 4,634,443 A | 1/1987 | Haber et al. |
| 4,669,478 A | 6/1987 | Robertson |
| 4,686,962 A | 8/1987 | Haber |
| 4,711,231 A | 12/1987 | Finegold et al. |
| 4,773,393 A | 9/1988 | Haber et al. |
| 4,779,611 A | 10/1988 | Grooters et al. |
| 4,784,660 A | 11/1988 | Fischell |
| 4,786,276 A | 11/1988 | Haber |
| 4,802,479 A | 2/1989 | Haber et al. |
| 4,817,637 A | 4/1989 | Hillegass et al. |
| 4,823,800 A | 4/1989 | Compos |
| 4,832,680 A | 5/1989 | Haber et al. |
| 4,846,784 A | 7/1989 | Haber |
| 4,857,041 A | 8/1989 | Annis et al. |
| 4,909,785 A | 3/1990 | Burton et al. |
| 4,938,760 A | 7/1990 | Burton et al. |
| 4,969,474 A | 11/1990 | Schwarz |
| 4,969,892 A | 11/1990 | Burton et al. |
| 4,991,588 A | 2/1991 | Pflueger et al. |
| 5,012,822 A | 5/1991 | Schwarz |
| 5,041,077 A | 8/1991 | Kulick |
| 5,041,136 A | 8/1991 | Wascher et al. |
| 5,047,055 A | 9/1991 | Bao et al. |
| 5,064,434 A | 11/1991 | Haber |
| 5,066,303 A | 11/1991 | Bark et al. |
| 5,097,848 A | 3/1992 | Schwarz |
| 5,112,303 A | 5/1992 | Pudenz et al. |
| 5,123,428 A | 6/1992 | Schwarz |
| 5,133,753 A | 7/1992 | Bark et al. |
| 5,149,052 A | 9/1992 | Stoy et al. |
| 5,154,187 A | 10/1992 | Brownlee |
| 5,156,157 A | 10/1992 | Valenta, Jr. et al. |
| 5,181,921 A | 1/1993 | Makita et al. |
| 5,192,326 A | 3/1993 | Bao et al. |
| 5,304,123 A | 4/1994 | Atala et al. |
| 5,308,323 A | 5/1994 | Sogawa et al. |
| 5,312,430 A | 5/1994 | Rosenbluth et al. |
| 5,313,934 A | 5/1994 | Wiita et al. |
| 5,320,617 A | 6/1994 | Leach |
| 5,334,153 A | 8/1994 | McIntyre et al. |
| 5,336,263 A | 8/1994 | Ersek et al. |
| 5,376,117 A | 12/1994 | Pinchuk et al. |
| 5,383,896 A | 1/1995 | Gershony et al. |
| 5,385,561 A | 1/1995 | Cerny |
| 5,411,475 A | 5/1995 | Atala et al. |
| 5,437,603 A | 8/1995 | Cerny et al. |
| 5,451,406 A | 9/1995 | Lawin et al. |
| 5,480,430 A | 1/1996 | Carlisle et al. |
| 5,483,976 A | 1/1996 | McLaughlin et al. |
| 5,496,271 A | 3/1996 | Burton et al. |
| 5,496,370 A | 3/1996 | Hamas |
| 5,499,994 A | 3/1996 | Tihon et al. |
| 5,518,504 A | 5/1996 | Polyak |
| 5,520,700 A | 5/1996 | Beyar et al. |
| 5,534,023 A | 7/1996 | Henley |
| 5,547,472 A | 8/1996 | Onishi et al. |
| 5,575,771 A | 11/1996 | Walinsky |
| 5,578,009 A | 11/1996 | Kraus et al. |
| 5,593,443 A | 1/1997 | Carter et al. |
| 5,607,441 A * | 3/1997 | Sierocuk ............ A61B 17/0218 606/198 |
| 5,624,395 A | 4/1997 | Mikhail et al. |
| 5,634,877 A | 6/1997 | Salama |
| 5,637,074 A | 6/1997 | Andino et al. |
| 5,647,836 A | 7/1997 | Blake, III et al. |
| 5,687,714 A | 11/1997 | Kolobow et al. |
| 5,749,826 A | 5/1998 | Faulkner |
| 5,803,901 A | 9/1998 | Chin et al. |
| 5,830,228 A | 11/1998 | Knapp et al. |
| 5,938,669 A | 8/1999 | Klaiber et al. |
| 5,964,806 A | 10/1999 | Cook et al. |
| 5,976,186 A | 11/1999 | Bao et al. |
| 6,005,020 A | 12/1999 | Loomis |
| 6,013,023 A | 1/2000 | Klingenstein |
| 6,021,781 A | 2/2000 | Thompson et al. |
| 6,033,413 A | 3/2000 | Mikus et al. |
| 6,039,686 A | 3/2000 | Kovac |
| 6,042,536 A | 3/2000 | Tihon et al. |
| 6,045,498 A | 4/2000 | Burton et al. |
| 6,050,937 A | 4/2000 | Benderev |
| 6,053,935 A | 4/2000 | Brenneman et al. |
| 6,063,093 A | 5/2000 | Winston et al. |
| 6,095,969 A | 8/2000 | Karram et al. |
| 6,099,547 A | 8/2000 | Gellman et al. |
| 6,110,101 A | 8/2000 | Tihon et al. |
| 6,110,191 A | 8/2000 | Dehdashtian et al. |
| 6,117,067 A | 9/2000 | Gil-Vernet |
| 6,120,539 A | 9/2000 | Eldridge et al. |
| 6,132,465 A | 10/2000 | Ray et al. |
| 6,167,886 B1 | 1/2001 | Engel et al. |
| 6,171,231 B1 | 1/2001 | Connolly |
| 6,221,005 B1 | 4/2001 | Bruckner et al. |
| 6,354,991 B1 | 3/2002 | Gross et al. |
| 6,387,043 B1 | 5/2002 | Yoon |
| 6,419,624 B1 | 7/2002 | Burton et al. |
| 6,419,701 B1 | 7/2002 | Cook et al. |
| 6,423,080 B1 | 7/2002 | Gellman et al. |
| 6,579,224 B1 | 6/2003 | Burton et al. |
| 6,645,138 B2 | 11/2003 | Cook et al. |
| 6,752,814 B2 | 6/2004 | Gellman et al. |
| 6,786,861 B1 | 9/2004 | Pretorius |
| 6,970,091 B2 | 11/2005 | Roe |
| 7,014,606 B2 | 3/2006 | Burton et al. |
| 7,322,360 B2 | 1/2008 | Fogarty et al. |
| 7,364,540 B1 | 4/2008 | Burton et al. |
| 7,395,822 B1 | 7/2008 | Burton et al. |
| 7,481,762 B2 | 1/2009 | Burton et al. |
| 7,647,113 B2 | 1/2010 | Wiribisky et al. |
| 7,744,913 B2 | 6/2010 | Noyes |
| 7,771,346 B2 | 8/2010 | Burton et al. |
| 7,828,716 B2 | 11/2010 | Burton et al. |
| 7,837,670 B2 | 11/2010 | Barath |
| 7,914,437 B2 | 3/2011 | Gozzi et al. |
| 8,926,494 B1 | 1/2015 | Cook et al. |
| 10,673,028 B2 | 6/2020 | Takei et al. |
| 2002/0010502 A1 | 1/2002 | Trachtenberg |
| 2002/0055748 A1 | 5/2002 | Gellman et al. |
| 2002/0156342 A1 | 10/2002 | Burton et al. |
| 2002/0185138 A1 | 12/2002 | Single et al. |
| 2003/0208222 A1 | 11/2003 | Zadno-Azizi |
| 2004/0015045 A1 | 1/2004 | Burton et al. |
| 2004/0230206 A1 | 11/2004 | Gellman et al. |
| 2004/0230207 A1 | 11/2004 | Gillman et al. |
| 2005/0027161 A1 | 2/2005 | Cook et al. |
| 2005/0228225 A1 | 10/2005 | Hauschild et al. |
| 2005/0256364 A1 | 11/2005 | Burton et al. |
| 2006/0025798 A1 | 2/2006 | Cook et al. |
| 2006/0241339 A1 | 10/2006 | Cook et al. |
| 2006/0281964 A1 | 12/2006 | Burton et al. |
| 2007/0197954 A1 | 8/2007 | Keenan |
| 2007/0276342 A1 | 11/2007 | Lin et al. |
| 2008/0156334 A1 | 7/2008 | Burton et al. |
| 2008/0167518 A1 | 7/2008 | Burton et al. |
| 2010/0261951 A1 | 10/2010 | Cook et al. |
| 2010/0292530 A1 | 11/2010 | Cook et al. |
| 2011/0124957 A1 | 5/2011 | Burton et al. |
| 2012/0029269 A1 | 2/2012 | Burton et al. |
| 2013/0237763 A1 | 9/2013 | Qiu |

(56) References Cited

U.S. PATENT DOCUMENTS

| | | | |
|---|---|---|---|
| 2015/0173708 A1 | 6/2015 | Cook et al. | |
| 2020/0261200 A1 | 8/2020 | Cook et al. | |
| 2021/0251736 A1 | 8/2021 | Cook et al. | |

FOREIGN PATENT DOCUMENTS

| | | |
|---|---|---|
| EP | 0078498 A1 | 6/1983 |
| EP | 0504934 A1 | 9/1992 |
| EP | 0639355 A1 | 2/1995 |
| EP | 0784987 A2 | 7/1997 |
| EP | 0941712 A1 | 9/1999 |
| EP | 1354568 A2 | 10/2003 |
| JP | 2022520268 | 3/2022 |
| WO | WO-9100069 A1 | 1/1991 |
| WO | WO-1991000069 A1 | 1/1991 |
| WO | WO-9601597 A2 | 1/1996 |
| WO | WO-9820812 A1 | 5/1998 |
| WO | WO-9835632 A1 | 8/1998 |
| WO | WO-9856311 A1 | 12/1998 |
| WO | WO-0018319 A1 | 4/2000 |
| WO | WO-0066030 A1 | 11/2000 |
| WO | WO-0126581 A1 | 4/2001 |
| WO | WO-2005082276 A1 | 9/2005 |
| WO | WO-2006091786 A1 | 8/2006 |
| WO | WO-2014140283 A1 | 9/2014 |
| WO | 2020168184 | 8/2020 |
| WO | 2020168184 | 11/2020 |

OTHER PUBLICATIONS

"U.S. Appl. No. 08/873,444, Final Office Action dated Sep. 27, 1999", 6 pgs.
"U.S. Appl. No. 08/873,444, Examiner Interview Summary dated Apr. 27, 1998", 2 pgs.
"U.S. Appl. No. 08/873,444, Final Office Action dated Aug. 5, 1998", 9 pgs.
"U.S. Appl. No. 08/873,444, Non-Final Office Action dated Jan. 13, 1998", 7 pgs.
"U.S. Appl. No. 08/873,444, Non-Final Office Action dated Feb. 4, 1999", 7 pgs.
"U.S. Appl. No. 08/873,444, Notice of Allowance dated Feb. 22, 1999", 2 pgs.
"U.S. Appl. No. 08/873,444, Response filed May 13, 1998 to Non-Final Office Action dated Jan. 13, 1998", 16 pgs.
"U.S. Appl. No. 08/873,444, Response filed Jul. 6, 1999 to Non-Final Office Action dated Feb. 4, 1999", 6 pgs.
"U.S. Appl. No. 08/873,444, Response filed Nov. 1, 1999 to Final Office Action dated Sep. 27, 1999", 2 pgs.
"U.S. Appl. No. 08/873,444, Response filed Nov. 5, 1998 to Final Office Action dated Aug. 5, 1998", 12 pgs.
"U.S. Appl. No. 08/873,444, Response filed Dec. 3, 1998 to Final Office Action dated Aug. 5, 1998", 9 pgs.
"U.S. Appl. No. 08/928,946, Non Final Office Action dated Jan. 13, 1999", 2 pgs.
"U.S. Appl. No. 08/928,946, Notice of Allowance dated May 3, 1999", 6 pgs.
"U.S. Appl. No. 08/928,946, Preliminary Amendment filed May 28, 1998", 6 pgs.
"U.S. Appl. No. 08/928,946, Response filed Feb. 16, 1999 to Non Final Office Action dated Jan. 13, 1999", 2 pgs.
"U.S. Appl. No. 08/928,946, Response filed Oct. 28, 2008 to Restriction Requirement dated Sep. 28, 2008", 3 pgs.
"U.S. Appl. No. 08/928,946, Restriction Requirement dated Sep. 28, 1998", 5 pgs.
"U.S. Appl. No. 09/345,884, Non-Final Office Action dated Mar. 19, 2001", 7 pgs.
"U.S. Appl. No. 09/345,884, Non-Final Office Action dated Sep. 29, 2000", 6 pgs.
"U.S. Appl. No. 09/345,884, Notice of Allowance dated Feb. 11, 2002", 5 pgs.
"U.S. Appl. No. 09/345,884, Notice of Allowance dated Sep. 24, 2001", 2 pgs.
"U.S. Appl. No. 09/345,884, Preliminary Amendment filed Apr. 12, 2000", 4 pgs.
"U.S. Appl. No. 09/345,884, Response filed Jul. 13, 2001 to Non-Final Office Action dated Mar. 19, 2001", 8 pgs.
"U.S. Appl. No. 09/345,884, Response filed Dec. 28, 2000 to Non-Final Office Action dated Sep. 28, 2000", 7 pgs.
"U.S. Appl. No. 09/415,801, Examiner Interview Summary dated May 22, 2002", 3 pgs.
"U.S. Appl. No. 09/415,801, Non-Final Office Action dated Mar. 27, 2001", 4 pgs.
"U.S. Appl. No. 09/415,801, Notice of Allowance dated Feb. 11, 2002", 6 pgs.
"U.S. Appl. No. 09/415,801, Notice of Allowance dated Oct. 9, 2001", 3 pgs.
"U.S. Appl. No. 09/415,801, Response filed Jul. 26, 2001 to Non-Final Office Action dated Mar. 27, 2001", 16 pgs.
"U.S. Appl. No. 09/416,193, Non-Final Office Action dated Mar. 27, 2001", 4 pgs.
"U.S. Appl. No. 09/416,193, Non-Final Office Action dated Jul. 15, 2002", 5 pgs.
"U.S. Appl. No. 09/416,193, Non-Final Office Action dated Oct. 10, 2001", 6 pgs.
"U.S. Appl. No. 09/416,193, Notice of Allowance dated Jan. 27, 2003", 5 pgs.
"U.S. Appl. No. 09/416,193, Response filed Apr. 9, 2002 to Non-Final Office Action dated Oct. 10, 2001", 15 pgs.
"U.S. Appl. No. 09/416,193, Response filed Jun. 26, 2001 to Non-Final Office Action dated Mar. 27, 2001", 14 pgs.
"U.S. Appl. No. 09/416,193, Response filed Nov. 15, 2002 to Non-Final Office Action dated Jul. 15, 2002", 5 pgs.
"U.S. Appl. No. 09/477,977, Advisory Action dated Aug. 21, 2002", 5 pgs.
"U.S. Appl. No. 09/477,977, Appeal Brief filed Feb. 10, 2003", 21 pgs.
"U.S. Appl. No. 09/477,977, Appeal Decision mailed Mar. 3, 2005", 10 pgs.
"U.S. Appl. No. 09/477,977, Examiner's Answer to Appeal Brief mailed May 7, 2003", 6 pgs.
"U.S. Appl. No. 09/477,977, Final Office Action dated Apr. 5, 2002", 8 pgs.
"U.S. Appl. No. 09/477,977, Final Office Action dated Jul. 15, 2005", 6 pgs.
"U.S. Appl. No. 09/477,977, Non-Final Office Action dated Feb. 27, 2007", 5 pgs.
"U.S. Appl. No. 09/477,977, Non-Final Office Action dated Apr. 7, 2006", 6 pgs.
"U.S. Appl. No. 09/477,977, Non-Final Office Action dated Aug. 2, 2001", 8 pgs.
"U.S. Appl. No. 09/477,977, Notice of Allowance dated Aug. 16, 2007", 4 pgs.
"U.S. Appl. No. 09/477,977, Notice of Allowance dated Sep. 22, 2006", 8 pgs.
"U.S. Appl. No. 09/477,977, Notice of Allowance dated Nov. 30, 2007", 2 pgs.
"U.S. Appl. No. 09/477,977, Preliminary Amendment filed Jan. 5, 2000", 1 pg.
"U.S. Appl. No. 09/477,977, PTO Response to Reply Brief mailed Jul. 22, 2003", 2 pgs.
"U.S. Appl. No. 09/477,977, Reply Brief filed Jul. 7, 2003", 2 pgs.
"U.S. Appl. No. 09/477,977, Response filed Jul. 7, 2006 to Non-Final Office Action filed Apr. 7, 2006", 10 pgs.
"U.S. Appl. No. 09/477,977, Response filed Jan. 2, 2002 to Non-Final Office Action dated Aug. 2, 2001", 5 pgs.
"U.S. Appl. No. 09/477,977, Response filed Jan. 16, 2006 to Final Office Action dated Jul. 15, 2005", 11 pgs.
"U.S. Appl. No. 09/477,977, Response filed Jul. 27, 2007 to Non-Final Office Action dated Feb. 27, 2007", 13 pgs.
"U.S. Appl. No. 09/477,977, Response filed Aug. 5, 2002 to Final Office Action filed Apr. 5, 2002", 20 pgs.
"U.S. Appl. No. 09/477,977, Supplemental Preliminary Amendment filed Apr. 26, 2000", 9 pgs.

(56) References Cited

OTHER PUBLICATIONS

"U.S. Appl. No. 09/561,551, 312 Amendment filed Feb. 27, 2008", 5 pgs.
"U.S. Appl. No. 09/561,551, Final Office Action dated Oct. 5, 2004", 5 pgs.
"U.S. Appl. No. 09/561,551, Final Office Action dated Oct. 31, 2006", 8 pgs.
"U.S. Appl. No. 09/561,551, Non-Final Office Action dated Feb. 22, 2006", 5 pgs.
"U.S. Appl. No. 09/561,551, Non-Final Office Action dated Apr. 5, 2005", 5 pgs.
"U.S. Appl. No. 09/561,551, Non-Final Office Action dated Apr. 17, 2007", 4 pgs.
"U.S. Appl. No. 09/561,551, Non-Final Office Action dated Jul. 9, 2001", 9 pgs.
"U.S. Appl. No. 09/561,551, Non-Final Office Action dated Dec. 18, 2003", 4 pgs.
"U.S. Appl. No. 09/561,551, Notice of Allowance dated Nov. 28, 2007", 2 pgs.
"U.S. Appl. No. 09/561,551, PTO Response to 312 Amendment dated Apr. 21, 2008", 2 pgs.
"U.S. Appl. No. 09/561,551, Response filed Jan. 5, 2005 to Final Office Action filed Oct. 5, 2004", 9 pgs.
"U.S. Appl. No. 09/561,551, Response filed Apr. 2, 2007 to Final Office Action filed Oct. 31, 2006", 10 pgs.
"U.S. Appl. No. 09/561,551, Response filed Jun. 17, 2004 to Non-Final Office Action filed Dec. 18, 2003", 8 pgs.
"U.S. Appl. No. 09/561,551, Response filed Aug. 22, 2006 to Non-Final Office Action filed Feb. 22, 2006", 11 pgs.
"U.S. Appl. No. 09/561,551, Response filed Sep. 6, 2005 to Non-Final Office Action filed Apr. 5, 2005", 8 pgs.
"U.S. Appl. No. 09/561,551, Response filed Sep. 17, 2007 to Non-Final Office Action filed Apr. 17, 2007", 8 pgs.
"U.S. Appl. No. 09/561,551, Response filed Nov. 9, 2001 to Non-Final Office Action filed Jul. 9, 2001", 20 pgs.
"U.S. Appl. No. 10/167,563, Final Office Action dated May 4, 2005", 6 pgs.
"U.S. Appl. No. 10/167,563, Non-Final Office Action dated Sep. 23, 2004", 5 pgs.
"U.S. Appl. No. 10/167,563, Notice of Allowance dated Oct. 4, 2005", 4 pgs.
"U.S. Appl. No. 10/167,563, Preliminary Amendment filed Jun. 11, 2002", 3 pgs.
"U.S. Appl. No. 10/167,563, Response filed Jan. 24, 2005 to Non-Final Office Action dated Sep. 23, 2004", 12 pgs.
"U.S. Appl. No. 10/167,563, Response filed Sep. 6, 2005 to Final Office Action dated May 4, 2005", 11 pgs.
"U.S. Appl. No. 10/167,565, Non-Final Office Action dated Feb. 11, 2003", 6 pgs.
"U.S. Appl. No. 10/167,565, Notice of Allowance dated May 30, 2003", 5 pgs.
"U.S. Appl. No. 10/167,565, Preliminary Amendment filed Jun. 11, 2002", 2 pgs.
"U.S. Appl. No. 10/167,565, Response filed May 9, 2003 to Non-Final Office Action dated Feb. 11, 2003", 7 pgs.
"U.S. Appl. No. 10/429,924, Final Office Action dated Dec. 13, 2006", 7 pgs.
"U.S. Appl. No. 10/429,924, Non-Final Office Action dated Mar. 17, 2008", 8 pgs.
"U.S. Appl. No. 10/429,924, Non-Final Office Action dated Mar. 23, 2006", 8 pgs.
"U.S. Appl. No. 10/429,924, Non-Final Office Action dated Jul. 5, 2007", 7 pgs.
"U.S. Appl. No. 10/429,924, Notice of Allowance dated Sep. 16, 2008", 4 pgs.
"U.S. Appl. No. 10/429,924, Preliminary Amendment filed May 5, 2003", 3 pgs.
"U.S. Appl. No. 10/429,924, Response filed Jun. 13, 2007 to Final Office Action dated Dec. 13, 2006", 8 pgs.
"U.S. Appl. No. 10/429,924, Response filed Aug. 5, 2008 to Non-Final Office Action dated Mar. 17, 2008", 10 pgs.
"U.S. Appl. No. 10/429,924, Response filed Sep. 22, 2006 to Non-Final Office Action dated Mar. 23, 2006", 10 pgs.
"U.S. Appl. No. 10/429,924, Response filed Dec. 5, 2007 to Non-Final Office Action dated Jul. 5, 2007", 10 pgs.
"U.S. Appl. No. 10/673,028, Non-Final Office Action dated Jun. 2, 2004", 4 pgs.
"U.S. Appl. No. 10/673,028, Preliminary Amendment filed Sep. 26, 2003", 3 pgs.
"U.S. Appl. No. 10/932,414, Advisory Action dated Aug. 12, 2008", 3 pgs.
"U.S. Appl. No. 10/932,414, Appeal Brief filed Oct. 21, 2008", 26 pgs.
"U.S. Appl. No. 10/932,414, Examiner's Answer to Appeal Brief mailed Mar. 2, 2009", 9 pgs.
"U.S. Appl. No. 10/932,414, Final Office Action dated Mar. 21, 2008", 7 pgs.
"U.S. Appl. No. 10/932,414, Final Office Action dated Jun. 15, 2007", 7 pgs.
"U.S. Appl. No. 10/932,414, Non-Final Office Action dated Feb. 12, 2007", 6 pgs.
"U.S. Appl. No. 10/932,414, Non-Final Office Action dated Apr. 17, 2006", 5 pgs.
"U.S. Appl. No. 10/932,414, Non-Final Office Action dated Sep. 14, 2007", 7 pgs.
"U.S. Appl. No. 10/932,414, Notice of Allowance dated Jan. 6, 2011", 4 pgs.
"U.S. Appl. No. 10/932,414, Notice of Allowance dated Oct. 23, 2006", 4 pgs.
"U.S. Appl. No. 10/932,414, Preliminary Amendment filed Sep. 2, 2004", 5 pgs.
"U.S. Appl. No. 10/932,414, Preliminary Amendment filed Dec. 14, 2004", 3 pgs.
"U.S. Appl. No. 10/932,414, PTO Response to 312 Amendment dated Apr. 19, 2011", 2 pgs.
"U.S. Appl. No. 10/932,414, Reply Brief filed May 4, 2009", 4 pgs.
"U.S. Appl. No. 10/932,414, Response filed May 14, 2007 to Non-Final Office Action dated Feb. 12, 2007", 8 pgs.
"U.S. Appl. No. 10/932,414, Response filed Jul. 7, 2006 to Non-Final Office Action dated Apr. 17, 2006", 7 pgs.
"U.S. Appl. No. 10/932,414, Response filed Jul. 18, 2008 to Final Office Action dated Mar. 21, 2008", 7 pgs.
"U.S. Appl. No. 10/932,414, Response filed Aug. 15, 2007 to Final Office Action dated Jun. 15, 2007", 7 pgs.
"U.S. Appl. No. 10/932,414, Response filed Dec. 14, 2007 to Non-Final Office Action dated Sep. 14, 2007", 8 pgs.
"U.S. Appl. No. 10/932,414, Supplemental Notice of Allowability dated Nov. 27, 2006", 2 pgs.
"U.S. Appl. No. 11/063,229, Advisory Action dated Nov. 13, 2009", 3 pgs.
"U.S. Appl. No. 11/063,229, Advisory Action dated Oct. 31, 2008", 3 pgs.
"U.S. Appl. No. 11/063,229, Examiner Interview Summary dated Apr. 9, 2008", 5 pgs.
"U.S. Appl. No. 11/063,229, Final Office Action dated Jul. 22, 2008", 11 pgs.
"U.S. Appl. No. 11/063,229, Final Office Action dated Sep. 2, 2009", 18 pgs.
"U.S. Appl. No. 11/063,229, Non Final Office Action dated Jun. 12, 2007", 10 pgs.
"U.S. Appl. No. 11/063,229, Non-Final Office Action dated Jan. 8, 2008", 10 pgs.
"U.S. Appl. No. 11/063,229, Non-Final Office Action dated Mar. 6, 2009", 12 pgs.
"U.S. Appl. No. 11/063,229, Non-Final Office Action dated Dec. 28, 2009", 12 pgs.
"U.S. Appl. No. 11/063,229, Response filed Apr. 8, 2008 to Non-Final Office Action filed Jan. 8, 2008", 8 pgs.
"U.S. Appl. No. 11/063,229, Response filed Jun. 8, 2009 to Non Final Office Action dated Mar. 6, 2009", 6 pgs.
"U.S. Appl. No. 11/063,229, Response filed Oct. 12, 2007 to Non-Final Office Action dated Jun. 12, 2007", 8 pgs.

(56) References Cited

OTHER PUBLICATIONS

"U.S. Appl. No. 11/063,229, Response filed Oct. 22, 2008 to Final Office Action dated Jul. 22, 2008", 8 pgs.
"U.S. Appl. No. 11/063,229, Response filed Nov. 2, 2009 to Final Office Action dated Sep. 2, 2009", 6 pgs.
"U.S. Appl. No. 11/120,631, Non-Final Office Action dated Aug. 24, 2006", 6 pgs.
"U.S. Appl. No. 11/120,631, Preliminary Amendment filed May 3, 2005", 1 pg.
"U.S. Appl. No. 11/331,838, Non-Final Office Action dated Jul. 22, 2009", 5 pgs.
"U.S. Appl. No. 11/331,838, Notice of Allowance dated Mar. 29, 2010", 9 pgs.
"U.S. Appl. No. 11/331,838, Preliminary Amendment filed Aug. 29, 2006", 6 pgs.
"U.S. Appl. No. 11/331,838, Response filed Dec. 22, 2009 to Non Final Office Action dated Jul. 22, 2009", 9 pgs.
"U.S. Appl. No. 11/361,016, Examiner Interview Summary dated Jan. 13, 2010", 4 pgs.
"U.S. Appl. No. 11/361,016, Final Office Action dated Sep. 4, 2009", 20 pgs.
"U.S. Appl. No. 11/361,016, Non-Final Office Action dated Jan. 21, 2009", 17 pgs.
"U.S. Appl. No. 11/361,016, Response filed May 21, 2009 to Non Final Office Action dated Jan. 21, 2009", 16 pgs.
"U.S. Appl. No. 11/622,384, Preliminary Amendment filed Jan. 11, 2007", 3 pgs.
"U.S. Appl. No. 12/051,515, Non-Final Office Action dated Mar. 24, 2010", 13 pgs.
"U.S. Appl. No. 12/051,515, Non-Final Office Action dated Oct. 9, 2009", 6 pgs.
"U.S. Appl. No. 12/051,515, Notice of Allowance dated Jul. 2, 2010", 5 pgs.
"U.S. Appl. No. 12/051,515, Response filed Feb. 5, 2010 to Non Final Office Action dated Oct. 9, 2009", 10 pgs.
"U.S. Appl. No. 12/051,515, Response filed May 7, 2010 to Non Final Office Action dated Mar. 24, 2010", 8 pgs.
"U.S. Appl. No. 12/054,662, Non-Final Office Action dated Jul. 9, 2009", 14 pgs.
"U.S. Appl. No. 12/411,806 , Response filed Apr. 5, 2012 to Non Final Office Action dated Oct. 6, 2011", 10 pgs.
"U.S. Appl. No. 12/411,806, Final Office Action dated Apr. 26, 2012", 17 pgs.
"U.S. Appl. No. 12/411,806, Final Office Action dated Aug. 16, 2013", 20 pgs.
"U.S. Appl. No. 12/411,806, Non Final Office Action dated Jan. 2, 2013", 18 pgs.
"U.S. Appl. No. 12/411,806, Non Final Office Action dated Apr. 10, 2014", 24 pgs.
"U.S. Appl. No. 12/411,806, Non Final Office Action dated Oct. 6, 2011", 17 pgs.
"U.S. Appl. No. 12/411,806, Notice of Allowance dated Sep. 2, 2014", 10 pgs.
"U.S. Appl. No. 12/411,806, Response filed Feb. 14, 2014 to Final Office Action dated Aug. 16, 2013", 13 pgs.
"U.S. Appl. No. 12/411,806, Response filed Jul. 2, 2013 to Non Final Office Action dated Jan. 2, 2013", 11 pgs.
"U.S. Appl. No. 12/411,806, Response filed Oct. 26, 2012 to Final Office Action dated Apr. 26, 2012", 11 pgs.
"U.S. Appl. No. 12/700,235 , Response filed Apr. 9, 2013 to Non Final Office Action dated Oct. 9, 2012", 10 pgs.
"U.S. Appl. No. 12/700,235, Examiner Interview Summary dated Dec. 6, 2013", 3 pgs.
"U.S. Appl. No. 12/700,235, Final Office Action dated Aug. 1, 2013", 17 pgs.
"U.S. Appl. No. 12/700,235, Non Final Office Action dated Oct. 9, 2012", 14 pgs.
"U.S. Appl. No. 12/838,927, Non Final Office Action dated Sep. 7, 2011", 4 pgs.
"U.S. Appl. No. 13/080,350, Non Final Office Action dated Aug. 15, 2013", 7 pgs.
"U.S. Appl. No. 14/589,361, Non Final Office Action dated Oct. 7, 2015", 10 pgs.
"U.S. Appl. No. 14/589,361, Preliminary Amdnedment filed Apr. 24, 2015", 5 pgs.
"Australian Application Serial No. 200521611 Examiner's report dated Dec. 8, 2009", 4 pgs.
"Canadian Application Serial No. 2,387,963, Office Action dated Feb. 20, 2007", 2 pgs.
"Canadian Application Serial No. 2,387,963, Office Action dated Nov. 14, 2007", 2 pgs.
"European Application Serial No. 05713846.3, Office Action dated Aug. 7, 2009", 4 pgs.
"European Application Serial No. 08075007.8, Extended European Search Report dated Oct. 30, 2009", 6 pgs.
"European Application Serial No. 08075007.8, Office Action dated Jul. 5, 2010", 1, pg.
"International Application No. PCT/US2005/005370, International Preliminary Report on Patentability dated Sep. 8, 2006", 8 pgs.
"International Application No. PCT/US2005/005370, International Search Report and Written Opinion dated Jun. 9, 2005", 13 pgs.
"International Application No. PCT/US98/12368, International Preliminary Examination Report dated Sep. 20, 1999", 6 pgs.
"International Application No. PCT/US98/12368, Written Opinion dated Mar. 19, 1999", 6 pgs.
"International Application Serial No. PCT/US2006/006546, International Search Report and Written Opinion dated Jun. 7, 2006", 12 pgs.
"International Application Serial No. PCT/US2020/018279, International Search Report dated May 25, 2020", 5 pgs.
"International Application Serial No. PCT/US2020/018279, Written Opinion dated May 25, 2020", 6 pgs.
Gregori, Andrea, et al., "Implantation of an Adjustable Continence Therapy System Using Local Anesthesia in Patients With Post-Radical Prostatectomy", (May 1, 2008), 5 Pgs.
Gregori, Andrea, et al., "Transrectal Ultrasound Guided Implantation of the PROACT Adjustable Continence Therapy System in Patients With Post-Radical Prostatectomy Stress Urinary Incontinence: A Pilot Study", The Journal of Urology, (Nov. 1, 2006), 5 pgs.
Gregori, Andrea, et al., "Transrectal Ultrasound-Guided Implantation of Adjustable Continence Therapy (PROACT): Surgical Technique and Clinical Results After a Mean Follow-up of 2 Years", (Nov. 30, 2009), 7 pgs.
Lima, S.V.C., "Further Experience with the Periurethral Expander: A New Type of Artificial Sphincter", British Journal of Urology (1997), 460-462.
Lima, Salvador C., et al., "Combined Use of Enterocystoplasty and a new Type of Artificial Sphincter in the Treatment of Urinary Incontinence", The Journal of Urology, 156(2 Pt 2), (Applicant notes that the attached cover sheet states "Papers Presented at Annual Meeting of the Section on Urology, American Academy of Pediatrics", San Francisco, CA Oct. 14-16, 1995), (Aug. 1996), 622-624.
"U.S. Appl. No. 17/302,529, Preliminary Amendment filed Jun. 16, 2021", 7 pages.
"International Application Serial No. PCT US2020 018279, International Preliminary Report on Patentability dated Aug. 26, 2021", 8 pgs.
"U.S. Appl. No. 16/450,246, Response filed Mar. 29, 2022 to Non Final Office Action dated Jan. 18, 2022", 14 pgs.
"U.S. Appl. No. 16/450,246, Final Office Action dated May 6, 2022", 17 pgs.
"U.S. Appl. No. 16/450,246, Response filed Jul. 1, 2022 to Final Office Action dated May 6, 2022", 13 pgs.
"U.S. Appl. No. 16/450,246, Notice of Allowance dated Jul. 27, 2022", 9 pgs.
U.S. Appl. No. 08/873,444 U.S. Pat. No. 6,045,498, filed Jun. 12, 1997, Implantable Device and Method for Adjustably Restricting a Body Lumen.

(56) References Cited

OTHER PUBLICATIONS

U.S. Appl. No. 09/477,977 U.S. Pat. No. 7,364,540, filed Jan. 5, 2000, Implantable Device and Method for Adjustably Restricting a Body Lumen.
U.S. Appl. No. 11/120,631, filed May 3, 2005, Implantable Device and Method for Adjustably Restricting a Body Lumen.
U.S. Appl. No. 11/622,384, filed Jan. 11, 2007, Implantable Device and Method for Adjustably Restricting a Body Lumen.
U.S. Appl. No. 12/051,515 U.S. Pat. No. 7,828,716, filed Mar. 19, 2008, Implantable Device and Method for Adjustably Restricting a Body Lumen.
U.S. Appl. No. 12/916,927, filed Nov. 1, 2010, Implantable Device and Method for Adjustably Restricting a Body Lumen.
U.S. Appl. No. 08/928,946 U.S. Pat. No. 5,964,806, filed Sep. 12, 1997, Adjustable Implantable Genitourinary Device.
U.S. Appl. No. 09/345,884 U.S. Pat. No. 6,419,701, filed Jul. 1, 1999, Adjustable Implantable Genitourinary Device.
U.S. Appl. No. 10/167,565 U.S. Pat. No. 6,645,138, filed Jun. 11, 2002, Adjustable Implantable Genitourinary Device.
U.S. Appl. No. 10/673,028, filed Sep. 26, 2003, Adjustable Implantable Genitourinary Device.
U.S. Appl. No. 10/932,414, filed Sep. 2, 2004, Adjustable Implantable Genitourinary Device.
U.S. Appl. No. 09/416,193 U.S. Pat. No. 6,579,224, filed Oct. 11, 1999, Apparatus and Method for Inserting an Adjustable Implantable Genitourinary Device.
U.S. Appl. No. 10/429,924 U.S. Pat. No. 7,481,762, filed May 5, 2003, Apparatus and Method for Inserting an Adjustable Implantable Genitourinary Device.
U.S. Appl. No. 09/415,801 U.S. Pat. No. 6,419,624, filed Oct. 11, 1999, Apparatus and Method for Inserting an Adjustable Implantable Genitourinary Device.
U.S. Appl. No. 10/167,563 U.S. Pat. No. 7,014,606, filed Jun. 11, 2002, Apparatus and Method for Inserting an Adjustable Implantable Genitourinary Device.
U.S. Appl. No. 11/331,833 U.S. Pat. No. 7,771,346, filed Jan. 13, 2006, Apparatus and Method for Inserting an Adjustable Implantable Genitourinary Device.
U.S. Appl. No. 12/838,927, filed Jul. 19, 2010, Apparatus and Method for Inserting an Adjustable Implantable Genitourinary Device.
U.S. Appl. No. 13/080,350, filed Apr. 5, 2011, Apparatus and Method for Inserting an Adjustable Implantable Genitourinary Device.
U.S. Appl. No. 12/411,806 U.S. Pat. No. 8,926,494, filed Mar. 26, 2009, Method and Apparatus for Placement of Implantable Device Adjacent a Body Lumen.
U.S. Appl. No. 14/589,361, filed Jan. 5, 2015, Method and Apparatus for Placement of Implantable Device Adjacent a Body Lumen.
U.S. Appl. No. 16/450,246, filed Jun. 24, 2019, Method and Apparatus for Monitoring Implantable Device for Urinary Continence.
"U.S. Appl. No. 16/450,246, Restriction Requirement dated Sep. 15, 2021", 6 pgs.
"U.S. Appl. No. 16/450,246, Response filed Nov. 12, 2021 to Restriction Requirement dated Sep. 15, 2021", 8 pgs.
"U.S. Appl. No. 16/450,246, Non Final Office Action dated Jan. 18, 2022", 18 pgs.
"European Application Serial No. 20714332.2, Response Filed Mar. 23, 2022 to Communication pursuant to Rules 161(1) and 162 EPC dated Sep. 21, 2021", 13 pgs.
"U.S. Appl. No. 17/302,529, Non Final Office Action dated Sep. 15, 2022", 11 pgs.
"Canadian Application Serial No. 3,130,302, Examiner's Rule 86(2) Requisition mailed Nov. 18, 2022, 6 pgs", 6 pgs.

\* cited by examiner

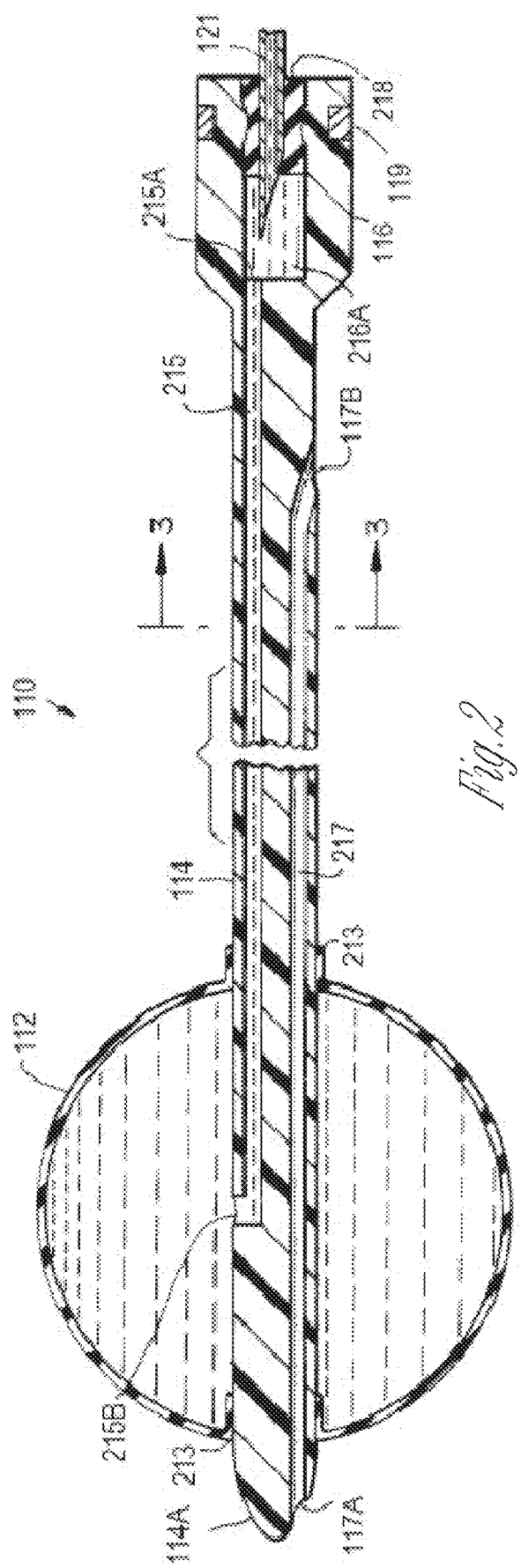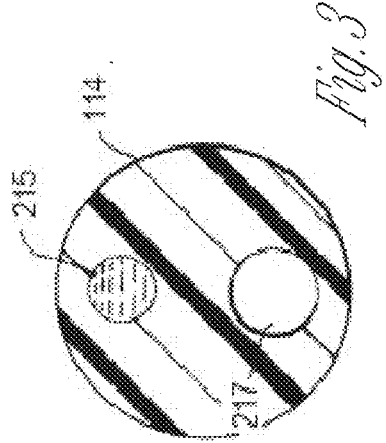

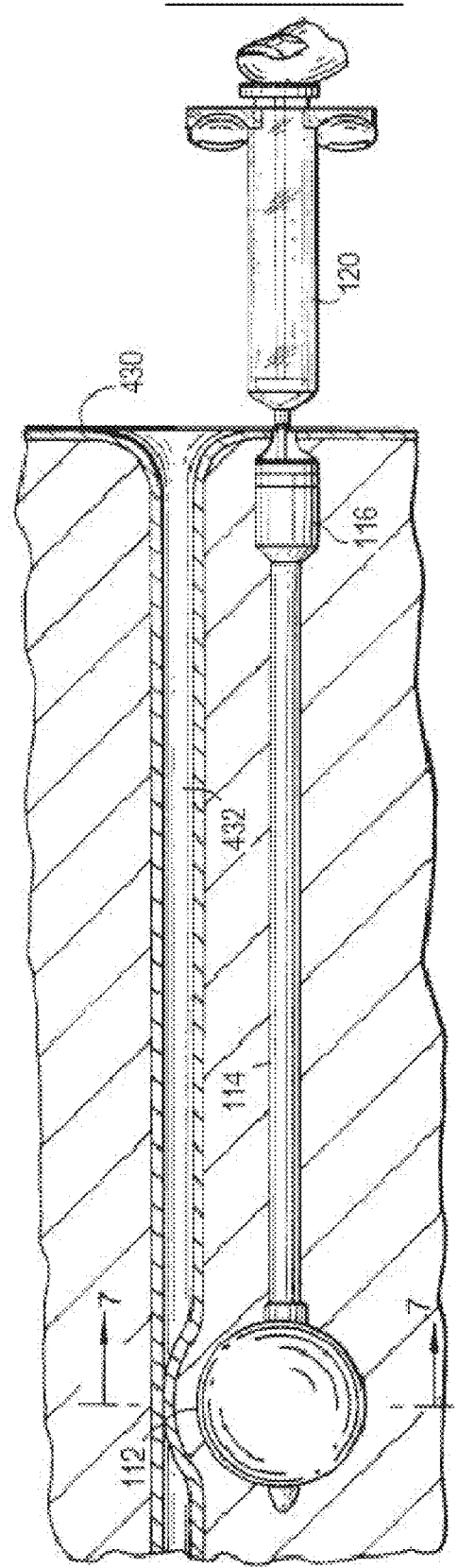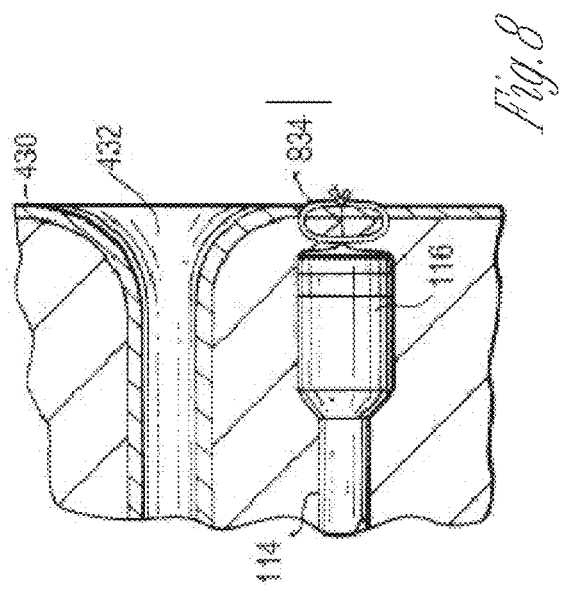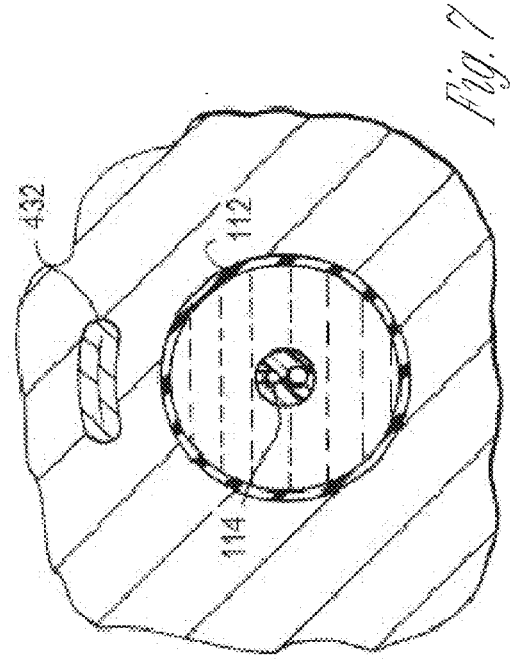

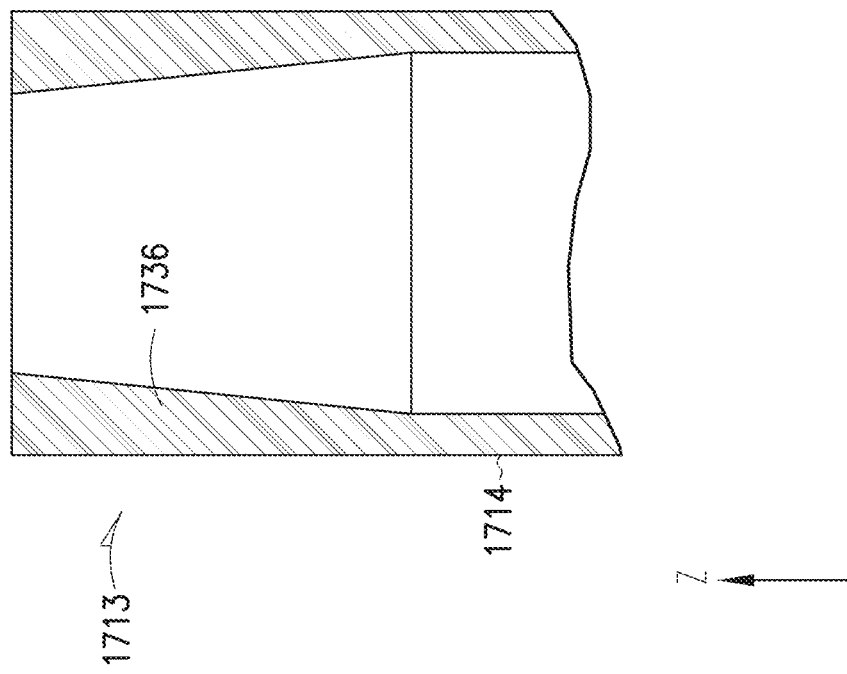
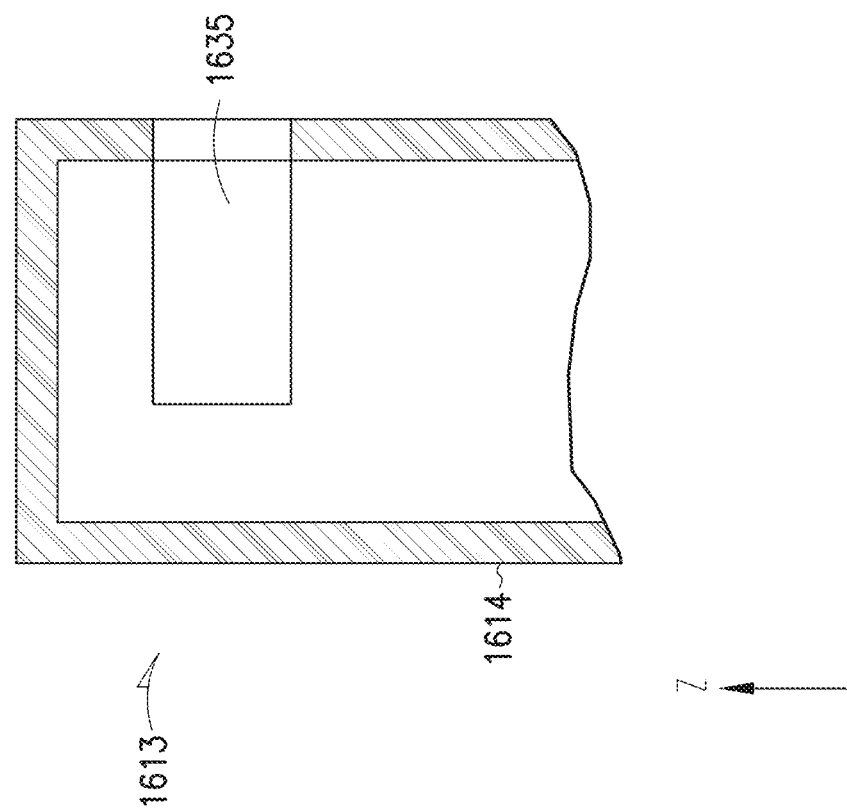

METHOD AND APPARATUS FOR MONITORING IMPLANTABLE DEVICE FOR URINARY CONTINENCE

CLAIM OF PRIORITY

This application is a continuation of U.S. patent application Ser. No. 16/450,246, filed Jun. 24, 2019, which claims the benefit of priority under 35 U.S.C. § 119(e) of U.S. Provisional Patent Application Ser. No. 62/805,503, entitled "METHOD AND APPARATUS FOR MONITORING URINARY INCONTINENCE IMPLANTABLE DEVICE", filed on Feb. 14, 2019, each of which are herein incorporated by reference in their entirety.

TECHNICAL FIELD

This document relates generally to implantable medical devices and more particularly to a method and system for monitoring placement and/or adjustment of an implantable devices for treating urinary incontinence.

BACKGROUND

An example of an implantable device for treating urinary incontinence includes an adjustable membrane element, such as a balloon, connected to a rear port with a conduit. The implantable device can be implanted in a patient with the adjustable membrane element placed adjacent to the patient's urethra and the rear port placed underneath the patient's skin by a minimally invasive surgery. The adjustable membrane element can be adjusted during and after the surgery by injecting fluid into the rear port or extracting fluid from the rear port percutaneously using a needle. In an exemplary treatment, two of such implantable devices are placed in the patient such that the two adjustable membrane elements provide pressure and support at the patient's bladder neck to protect against accidental leaking of urine during sneeze, cough, or physical activity. The efficacy of this treatment depends on proper placement in the patient and adjustment of the adjustable membrane element after the placement.

SUMMARY

One or more sensors are incorporated onto one or more of an implantable device and a surgical tool used for placement and/or adjustment of the implantable device. The implantable device includes an adjustable membrane element for controllable coaptation of a body lumen, such as coaptation of a urethra as treatment for urinary incontinence. In various embodiments, the one or more sensors can be configured to detect information indicative of at least one of a shape of the adjustable membrane element, a position of the adjustable membrane element relative to the body lumen, or a shape of the body lumen.

In various embodiments, an implantable device for controllable coaptation of a body lumen can include an adjustable membrane element and an elongate conduit. The adjustable membrane element can include a continuous wall having an inner surface defining a chamber. The elongate conduit can include a peripheral surface connected to and sealed to the adjustable membrane element, a rear end, a front end, and a lumen extending longitudinally in the elongate conduit from a first opening at the rear end to a second opening in fluid communication with the chamber of the implantable device for adjustably expanding or contracting the adjustable membrane element by applied flowable material introduced through the first opening. One or more sensors can be incorporated into the implantable device and/or a sensor probe for monitoring positioning of the implantable device, adjustment of the implantable device, and/or state of coaptation of the body lumen. In one embodiment, one or more sensors are incorporated onto at least one of the adjustable membrane element or the elongate conduit of the implantable device. In another embodiment, a sensor probe includes a front end into which a sensor incorporated. In one embodiment, the lumen of the elongate conduit is configured to accommodate a portion of the sensor probe including its front end. In another embodiment, the implantable device includes another lumen extending longitudinally in the elongate conduit and having an inlet configured to receive a portion of the sensor probe and a closed end to stop the sensor probe or an outlet configured to allow a portion of the sensor probe including its front end to exit. In various embodiments, the one or more sensors can include one or more optical sensors, such as cameras or borescopes, and/or one or more ultrasonic transducers for producing an ultrasonic image.

This summary is an overview of some of the teachings of the present application and not intended to be an exclusive or exhaustive treatment of the present subject matter. Further details about the present subject matter are found in the detailed description and appended claims. The scope of the present invention is defined by appended claims and their legal equivalents.

BRIEF DESCRIPTION OF THE DRAWINGS

FIG. 2 is a longitudinal cross-sectional view of the implantable device shown in FIG. 1, according to an embodiment of the present subject matter.

FIG. 3 is a cross-sectional view taken along line 3-3 of FIG. 2, according to an embodiment of the present subject matter.

FIG. 6 shows the implanted device after being expanded at the desired location in the body tissue of the patient to displace body tissue toward the body lumen for causing adjustable restriction of the body lumen, according to an embodiment of the present subject matter.

FIG. 7 is a cross-sectional view taken along line 7-7 of FIG. 6, according to an embodiment of the present subject matter.

FIG. 8 shows the implantable device after being inserted with its rear port underneath the skin of a patient, according to an embodiment of the present subject matter.

FIG. 16 is a cross-sectional view of a portion of a front end of an implantable device, according to an embodiment of present subject matter.

FIG. 17 is a cross-sectional view of a portion of a front end of an implantable device, according to an embodiment of present subject matter.

DETAILED DESCRIPTION

Figure 1:
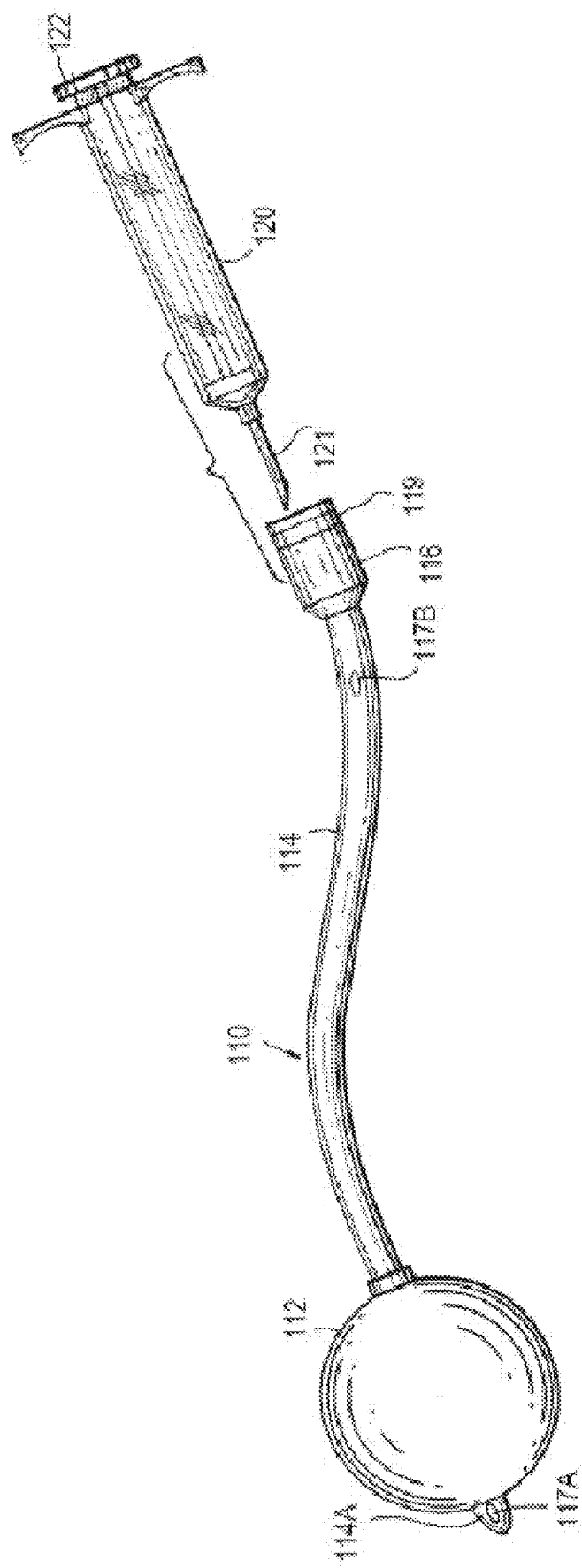
FIG. 1 is a perspective view of an implantable device and a syringe source for providing a flowable material to an adjustable membrane element of the implantable device, according to an embodiment of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

This document discusses, among other things, a system and method for monitoring placement and/or adjustment of an implantable device for treating urinary incontinence. The implantable device can include, for example, an adjustable membrane element connected to a rear port with a conduit that has a lumen providing for fluid communication between a chamber of the adjustable membrane element and an interior cavity of the rear port. Various structural elements of the implantable device (e.g., the implantable device 110 shown in FIG. 1) discussed in this document may each be referred to by various terms. The "adjustable membrane element" (e.g., the adjustable membrane element 112 shown in FIG. 1) can also be referred to as, for example, an adjustable element, an expandable element, an expandable membrane element, a forward expandable membrane element, a balloon, or an adjustable balloon. The "conduit" (e.g., the conduit 114 shown in FIG. 1) can also be referred to as, for example, a central conduit element, a device conduit, a connecting conduit, a connecting conduit tube, or a tubular elongate body. The "rear port" (e.g., the rear port 116 shown in FIG. 1) can also be referred to as, for example, a rearward port portion or a rear port element. The "lumen" (e.g., the first lumen 215 and the second lumen 217 shown in FIG. 2) can also be referred to as, for example, a passageway, an inner passageway, or an interior passageway.

In an example, the implantable device includes an adjustable balloon connected to a port with a conduit. The balloon is placed adjacent the urethra to exert non-circumferential compression upon the urethral wall. The effectiveness of the therapy depends on proper positioning of the balloon in a patient's body, such as in retropubic space (resulting from a radical prostatectomy) near the urethra-vesical anastomosis above the urogenital diaphragm in close proximity to the urethral walls. When two balloons (e.g., of two implantable devices) are used, their preferred positioning is usually symmetrical and lateral with respect to the urethra. Fluoroscopy or transrectal ultrasonography can be used to visually monitor the positioning of the balloon(s) during the implantation of the implantable device(s). Fluoroscopy has become a standard technique, but exposes the patient to radiation and provides a two-dimensional view that presents viewing difficulties under some circumstances. For examples, when the patient is on operation table, the fluoroscopic image does not show the location of the balloons on the anterior-posterior plane, and therefore does not show whether the balloons are properly positioned to exert compression upon the urethral wall. Transrectal ultrasonography (FRITS) can provide for better viewing (e.g., the location of the balloons on the anterior-posterior plane) but requires the surgeon to be familiar with this imaging technique, During an implantable process, implantable device(s) are initially placed in the patient with the balloon(s) positioned in the target space(s). The balloon(s) can be left slightly inflated to allow for encapsulation (by the patient's tissue) without migration from the target space(s). After the encapsulation, the patient will go through one or more adjustment procedures during which the balloon(s) are adjusted to obtain and maintain urinary continence without causing undesirable obstruction.

The present subject matter uses one or more sensors incorporated onto the implantable device and/or a surgical tool for implanting the implantable device to monitor the placement and/or adjustment of the implantable device(s). This monitoring technique avoids use of fluoroscopy or transrectal ultrasonography and their disadvantages such as exposure to x-ray or rectal insertion of ultrasonic probe. In one embodiment, the one or more sensors include one or more ultrasonic transducers on the implantable device and/ or the surgical tool allow for ultrasonic imaging to be used to monitor the placement and adjustment of the balloon(s) during device implantation. The ultrasonic sensor(s) on the implantable device can further allow for post-operative adjustment of the balloon(s).

In various embodiments, the present subject matter provides sensing means for monitoring, for example, location of each balloon and amount of inflation (expansion) of each balloon. In various embodiments, the sensing means can also be used for monitoring various states of the urethra that can indicate an amount of compression resulting from a degree of expansion of the balloon, such as excessive compression resulting from over-inflation of the balloon, adequate compression (target of the treatment), and insufficient compression resulting from under-inflation of the balloon. The target of the treatment is to provide the patient with continence without undesirable obstruction, and this requires the right amount of coaptation of the urethra resulting from placing the balloon(s) in the right position(s) and giving each balloon the right amount of inflation. The present subject matter allows for determination of the right position and right amount of inflation for each balloon.

FIGS. 1-10 illustrate various embodiments of an implantable medical device and a surgical tool. The surgical tool includes an elongate body and can be used as a base device onto which the one or more sensors can be incorporated. The implantable medical device can be used with the surgical tool including the sensor(s), or can be used as a base device onto which the one or more sensors can be incorporated. The various embodiments of the implantable device and the surgical tool are illustrated in FIGS. 1-10 and discussed below by way of example, and not by way of restriction. These examples as well as additional examples of the implantable device and the surgical tool are discussed in U.S. Pat. Nos. 5,964,806, 6,045,498, 6,419,624, 6,579,224, and 8,926,494, all assigned to UroMedica, Inc., which are incorporated by reference herein in their entireties. FIGS. 11-23 illustrate various embodiments of the one or more sensors incorporated onto an implantable device and/or a surgical tool such as those discussed in the document.

According to the present subject matter as shown by FIG. 1, there is provided an elongate implantable device 110, which includes an adjustable membrane element 112 shown in its full expanded size, and is attached pressure-tightly to an elongate conduit 114, which is connected to a rear port 116 communicating with the expandable element 112 through a first lumen 215 (see FIG. 2). The conduit 114 has a pointed forward end 114A which extends slightly beyond the expandable element 112. A syringe 120 including a hollow needle 121 and a rear axially-movable plunger 122 is provided for adjustably injecting a suitable flowable material into the implantable device 110 through the rear port 116 to expand the adjustable membrane element 112.

As further shown in FIGS. 2 and 3, the conduit 114 contains two elongate lumens or passageways. The first lumen 215 provides an internal passage by which the flowable material is directed from a cavity 216A in the rear port 116 to expand the adjustable membrane element 112. The conduit 114 is attached integrally to the rear port 116 at its rearward end. A second lumen 217 extends from a front opening 117A to a rearward opening 117B and serves to receive an elongate guide probe (see FIG. 4) and effect delivery of the implantable device 110 to a desired location in the body tissue of a patient.

An important feature of the implantable device 110 having the first lumen 215 includes a first opening port 215A located in cavity 216A of the rear port 116 between an elastic septum 218 and the conduit 114 and is connected to the first lumen 215, so that a flowable material can be infused therethrough, and a second port 215B serves to direct the working fluid to the adjustable membrane element 112. During adjustment of the volume of the membrane fluid provided from a hollow needle 121 of syringe 120, is infused through the septum 218 and continues through the conduit 114 connected to the adjustable membrane element 112. The rear port 116 preferably has a diameter greater than conduit 114 to accommodate the cavity 216A and the septum 218, which is retained securely by a clamp ring 119.

The entire implantable device 110 including the adjustable membrane element 112 is formed of a biocompatible material such as silicone or polyurethane elastomer, and the conduit 114 and the rear port 116 may be formed as a unitary construction. Optionally, the adjustable membrane element 112, the rear port 116, and the conduit 114 can be molded as one piece. As shown in FIG. 2, the adjustable membrane element 112 is adhered at 213 to conduit tube 114 at its forward end by a suitable adhesive material.

Figure 4:
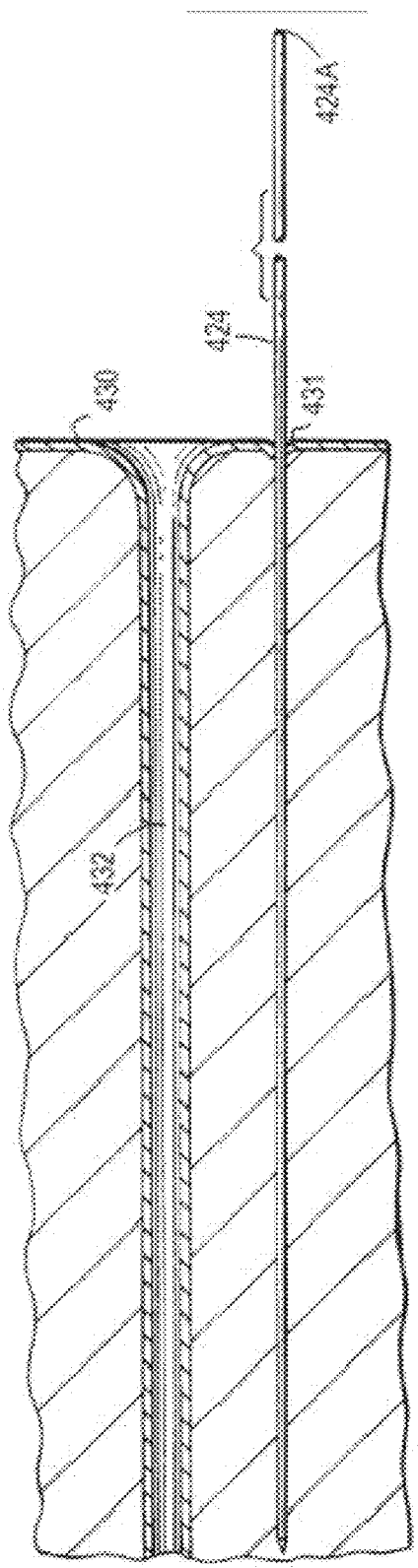
FIG. 4 illustrates a guide probe inserted into body tissue to an implant location adjacent a body lumen of a patient prior to insertion of the implantable device, according to an embodiment of the present subject matter.
Figure 5:
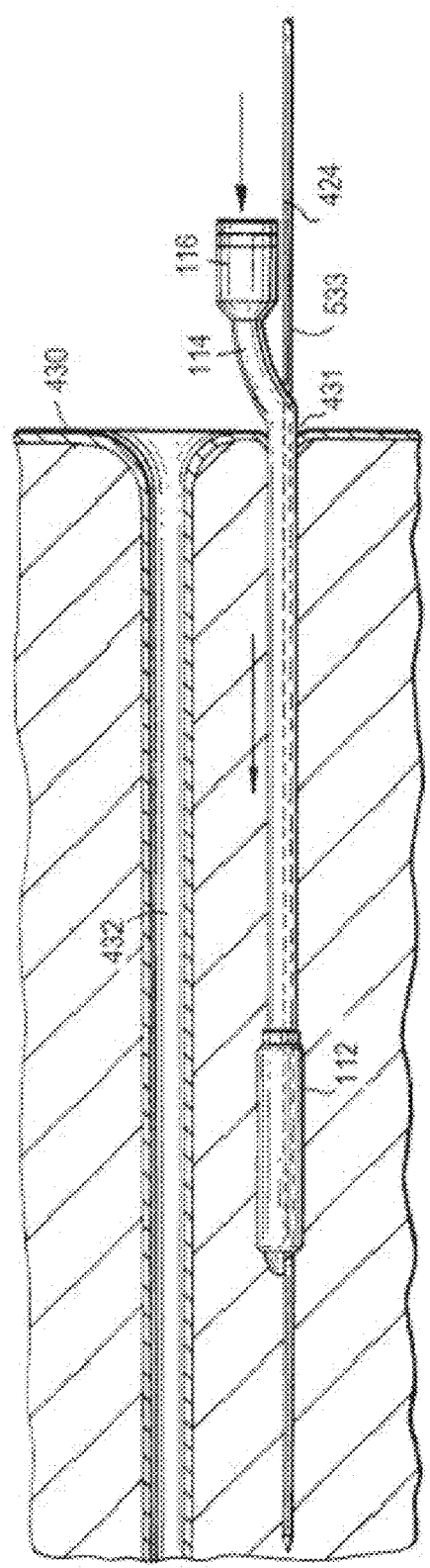
FIG. 5 shows the implantable device placed over the guide probe and partially advanced to the desired location with the adjustable membrane element being deflated, according to an embodiment of the present subject matter.

The implantable device and assembly according to the present subject matter can include three main members. The first member provided is an elongate guide in the form of a stiff solid elongate guide probe 424 (see FIG. 4) configured for delivery of the implantable device 110 to the desired site in the body tissue of a patient as generally shown by FIGS. 4 and 5. Alternatively, the elongate guide member can be in the form of a flexible guidewire which has been initially delivered into the body tissue through a separate hollow stiff probe that has been inserted to the desired location in the body tissue. The second member of the assembly is the implantable device 110 which includes the adjustable membrane element 112, the conduit 114 containing the two lumens 215 and 217, and the rear port 116. During its implantation, the implantable device 110 is guided to a pre-determined location adjacent a body lumen in a patient's body after the elongate solid guide probe 424 is first surgically inserted into the body tissue of the patient to establish an initial pathway. The lumen forward end opening 117A of the implantable device 110 is then disposed over the rear end of the guide probe 424 to guide the implantable device 110 and deliver the adjustable membrane element 112 (in its contracted shape) to the pre-determined location in the body tissue adjacent to the lumen which is to be adjustably restricted. The diameter of the second lumen 217 is made slightly larger than that of the guide probe 424 to permit the implantable device 110 to slide easily over the probe member.

During the implantation of the implantable device 110, a physician can first make a small incision in the skin 430 of the patient near a body lumen 432 that needs to be restricted, and then by visualization means such as fluoroscopy or ultrasonic imaging, the solid guide probe 424 is directed to the desired location, depending upon the anatomy of the patient. Thereafter, the opening 117A of the second lumen 117 of the conduit 114 with the adjustable membrane element 112 in its initial deflated or contracted condition, is slid over the rear end 424A of the guide probe 424. The guide probe 424 slides through the second lumen 217 of the conduit 114 and exits at the rearward opening 117B. As illustrated in FIG. 2, the opening 117B is between the adjustable membrane element 112 and the rear port 116, However, it may be advantageous to locate the opening 117B close to the adjustable membrane element 112 or, alternatively, to have the second lumen 217 extend through the rear port 116.

If desired, a mark 533 can be provided on the guide probe 424 which when aligned with a feature on the implantable device 110 such as the rear port 116 can assure that the implantable device 110 is appropriately placed at the correct depth in the patient's body tissue 430. It may be necessary to provide the conduit 114 in multiple lengths to facilitate placement of the septum 218 near the patient's skin. Alternatively, an effective length of the conduit 114 can be made adjustable by it having a helical shape similar to that of a coiled spring.

After the implantable device 110 has been advanced over guide probe 424 so that the contracted adjustable membrane element 112 is in the desired position adjacent to the body lumen 432, the body lumen 432 may be restricted to a desired degree by piercing septum 218 with the needle 121 of syringe 120 and injecting a flowable material through the first lumen 215 into the adjustable membrane element 112. The physician can determine the desired degree of restriction of body lumen 432 by means such as infusing fluid through the body lumen past the restriction and measuring the back pressure.

As illustrated by FIGS. 1 and 6, the source of flowable material is usually a syringe 120 with a hollow needle used to pierce the elastic septum 218. However, alternate fluid containers with means for making a reversible connection to the implantable device 110 could be used. The flowable material may be, for example, a saline solution, a flowable gel, or a slurry of particles in a liquid carrier. It may be advantageous to make the flowable material radiopaque so that the degree of membrane inflation may be viewed by x-ray.

An alternative method of delivery of the implantable device 110 can be to first withdraw the guide probe 24 from the body tissue and then inflate the adjustable membrane element 112. A further alternative would be to first place the implantable device 110 over the solid guide probe 424 outside the body and then insert them both into the body tissue as a unit. To facilitate this latter procedure, it may be desirable that there be some friction between the solid guide probe 424 and the second lumen 217 in the conduit 114.

After the implantable device 110 has been properly positioned with the adjustable membrane element 112 located near the body lumen 432 and the septum 218 in the rear port 116 located near the skin 430, the device is injected with a flowable material from the syringe 120. The expandable member can be inflated to a certain extent and then deflated to an extent suitable for encapsulation of the expandable member by body tissue. The guide probe 24 is then withdrawn from the device, leaving the slightly expanded membrane element in the body tissue. Then the skin incision 431 is closed over the port 116 by means such as a suture 834 as shown in FIG. 8.

The present subject matter provides the implantable device 110 with adjustability of the membrane expansion post-operatively. This adjustability is effected because the septum 218 is located remote from the adjustable membrane element 112 but near and under the patient's skin. The port and septum is located by, for instance, manual palpation of the skin region and the needle of the syringe is inserted through the skin and septum to add or remove material from the expandable member, thus increasing or decreasing the restriction of the body lumen.

To assure proper sealing of the septum 218, it is placed in compression within a cavity 216A by providing a tight metal ring 119 that surrounds the rear port 116 and is smaller in diameter than the port. When the needle 121 of the syringe 120 is withdrawn from the septum 218 after expansion or adjustment of the adjustable membrane element 112, there is positive sealing around the perimeter of the septum 218.

FIGS. 4-8 generally illustrate the method or procedure for properly implanting the implantable device 110 into the body tissue of a patient. As shown by FIG. 4, a physician, after locating the body lumen such as a urethra of the patient, makes a small incision 431 and inserts the guide probe 424 in the body tissue to a desired location adjacent the body lumen 432. This procedure is usually carried out under a local anesthetic with visual guidance, for instance under fluoroscopy, by the physician. Next, the physician takes the implantable device 110 and places it over the guide probe 424 through the second lumen 217 as shown in FIGS. 1 and 2, The guide probe 424 enters the rear opening 117B and exits the forward opening 117A. The implantable device 110, with the conduit 114 being sufficiently flexible, is advanced along the guide probe 424 into the body tissue.

After the desired location within the body tissue has been reached, a suitable flowable material is introduced into the implantable device 110 from a source such as the syringe 120 having hollow needle 121 inserted through septum 218 to at least partially expand the adjustable membrane element 112, as shown by FIG. 6. Next, the guide probe 424 is removed and the adjustable membrane element 112 is expanded further to the desired enlarged size for restriction of the body lumen 432. The syringe 120 is removed from the implantable device 110, after which the desired size of the adjustable membrane element 112 is maintained by the elastic septum 218. Next, the patient's incision at 431 is surgically closed over the port 116 and septum 218 by sutures at 834.

Figure 9:
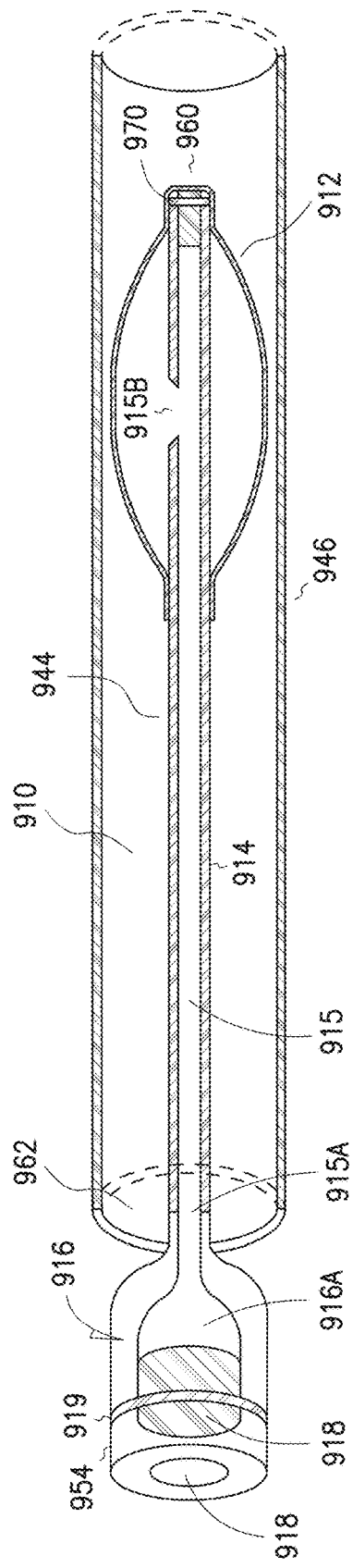
FIG. 9 is a schematic of another implantable device, according to an embodiment of the present subject matter.

FIG. 9 is an illustration of an implantable device kit 940, showing a cross-sectional view, according to one embodiment of the present subject matter. The implantable device kit 940 includes an implantable device 910 having an adjustable membrane element 912 and an elongate conduit 914, where the conduit 914 includes at least a first lumen 915 which extends longitudinally in the conduit 914 from a first opening 915A at a rear end (also referred to as a proximal end) 962 to a second opening 915B, and where the implantable device 910 is shown positioned within a channel 944 of a sheath 946.

The implantable device kit 940 further includes a rear port 916, where the rear port 916 is coupled to the rear end 962 of the conduit 914. In one embodiment, the rear port 916 is coupled to the rear end 962 of the elongate body 914 using chemical adhesives, or alternatively, using sonic welding techniques as are known in the art. In an additional embodiment, the rear port 916 and rear end 962 are formed together in a polymer molding process, such as liquid injection molding, as are known in the art.

The rear port 916 includes a cavity 916A, Where the cavity 916A is in fluid communication with the first opening 915A of the conduit 914. In one embodiment, the rear port 916 also includes an elastic septum 918 through which the cavity 916A is accessed, where the elastic septum 918 is a sealable after repeated pierces, for example, with a needle. In one embodiment, the elastic septum 918 is retained in the rear port 916 by a clamp ring 919 located around the rear port 916. In one embodiment, the clamp ring 919 is made of a biocompatible material, such as, for example, titanium. In one embodiment, the elastic septum 918 is made of a biocompatible material, such as, for example, silicone or polyurethane. The rear port 916 has an outer diameter defined by an outer surface 954 of the rear port 916. In one embodiment, the rear port 916 has an outer diameter of 1 to 15 millimeters, with 4.5 millimeters being a specific example.

In one embodiment, the outer surface of the rear port 916 and the adjustable membrane element 912 are of a size (e.g., a diameter) that is smaller than an inner size (e.g., a diameter) of the channel 944 to allow the implantable device 910 to be moved longitudinally through the channel 944 of the sheath 946. In an alternative embodiment, the rear port 916 is constructed of at least one material flexible enough to allow the size of the rear port 916 in its relaxed state to be compressed to a size sufficiently small so that the implantable device 910 can be moved longitudinally through the channel 944 of the sheath 946. In various embodiments, the conduit 914 has a stiffness sufficient to allow force applied at the rear end of its tubular elongate body to move the implantable device 910 at least partially through the channel 944 of the sheath 946. In one embodiment, the stiffness of the conduit 914 is determined based on the type of material used in constructing its tubular elongate body. Alternatively, support elements can be added to the tubular elongate body. For example, a metal coil can be placed longitudinally within the tubular elongate body to increase the stiffness of the tubular elongate body.

Once the implantable device 910 is positioned within a body, the adjustable membrane element 912 is inflated by releasably connecting a flowable material source to the rear port 916. In one embodiment, the flowable material source includes a syringe with a non-coring needle, where the needle is inserted through the elastic septum 918. A measured supply of fluid volume can be introduced into the implantable device 910, and the adjustable membrane element 912 expands or contracts due to a volume of flowable material introduced into the cavity 916A of the rear port 916 from the flowable material source. The adjustable membrane element 912 is then used to at least partially and adjustably restrict the body lumen. Fluids suitable for infusing into the prosthesis include, but are not limited to, sterile saline solutions, polymer gels such as silicone gels or hydrogels of polyvinylpyrrolidone, polyethylene glycol, or carboxy methyl cellulose for example, high viscosity liquids such as hyaluronic acid, dextran, polyacrylic acid, polyvinyl alcohol, or a radio-opaque fluid for example. Once the adjustable membrane element 912 has been inflated, the needle is withdrawn from the septum of the rear port 916. In an additional embodiment, a detectable marker 970 is imbedded in the continuous wall of the adjustable membrane element 912. The detectable marker 970 allows the adjustable membrane element 912 to be located within the tissues of a patient using any number of visualization techniques which employ electromagnetic energy as a means of locating objects within the body. In one embodiment, the detectable marker 970 is constructed of tantalum and the visualization techniques used to visualize the adjustable membrane element 912 are x-ray or fluoroscopy as are known in the art.

In an additional embodiment, a detectable marker is imbedded in the implantable device 910. For example, the detectable marker 970 is located at a front end (also referred to as a distal end) 960 (e.g., the tip) of the conduit 914. Alternatively, the detectable marker can be located in the continuous wall of the adjustable membrane element 912. The detectable marker 970 allows the front end 960, or the adjustable membrane element 912, to be located within the tissues of a patient using any number of visualization techniques which employ electromagnetic energy as a means of locating objects within the body. In one embodiment, the detectable marker 970 is constructed of tantalum and the visualization techniques used to visualize the front end 960, or the adjustable membrane element 912, are x-ray or fluoroscopy as are known in the art. In an additional embodiment, the sheath could also have a detectable marker, where the marker could be incorporated into, or on, the wall of the sheath. Alternatively, the entire sheath could be constructed to be radio-opaque.

Figure 10:
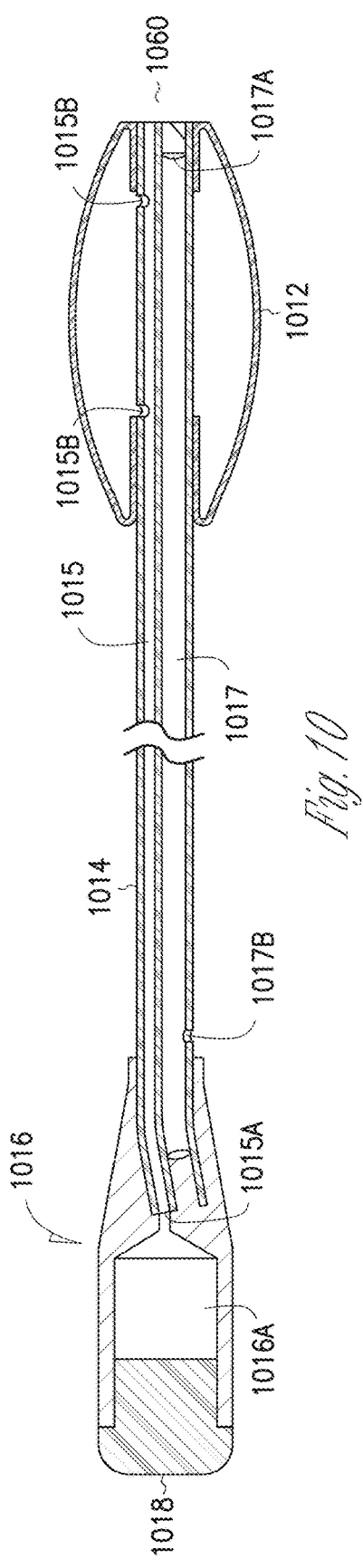
FIG. 10 is a schematic of another implantable device, according to an embodiment of the present subject matter.

FIG. 10 is an illustration of an additional embodiment of an implantable device 1010 according to the present subject matter. The implantable device 1010 includes an adjustable membrane element 1012 and a conduit 1014. The conduit 1014 has a front end 1060. In one embodiment, the peripheral surface of the conduit 1014 is connected to and sealed to the adjustable membrane element 1012. In one embodiment, the adjustable membrane element 1012 includes a continuous wall having an inner surface defining a chamber.

The conduit 1014 includes a first lumen 1015 and a second lumen 1017. In one embodiment, the first lumen 1015 extends longitudinally in the conduit 1014 from a first opening 1015A to one or more second openings 1015B (e.g., two openings as shown in FIG. 10). The second opening(s) 1015B is in fluid communication with the chamber of adjustable membrane element 1012 for adjustably expanding or contracting the adjustable membrane element 1012 by flowable material introduced through the first opening 1015A.

The second lumen 1017 extends longitudinally along the conduit 1014 from an inlet 1017B to a closed end 1017A at the front end 1060. In one embodiment, the second lumen 1017 and the inlet 1017B are each of sufficient diameter to receive a push rod that can be used to advance the implantable device 1010 in the tissue.

The implantable device 1010 further includes a rear port 1016, which is coupled to the rear end of the conduit 1014. In one embodiment, the rear port 1016 is similar to the rear port 916 and includes a cavity 1016A and an elastic septum 1018. The cavity 1016A coupled to and in fluid communication with the first lumen 1015 at the first opening 1015A. The elastic septum 1018 allows for excess to the cavity 1016A using a needle, for introducing and/or withdrawing fluid to expand and/or extract the adjustable membrane element 1012.

Figure 11:
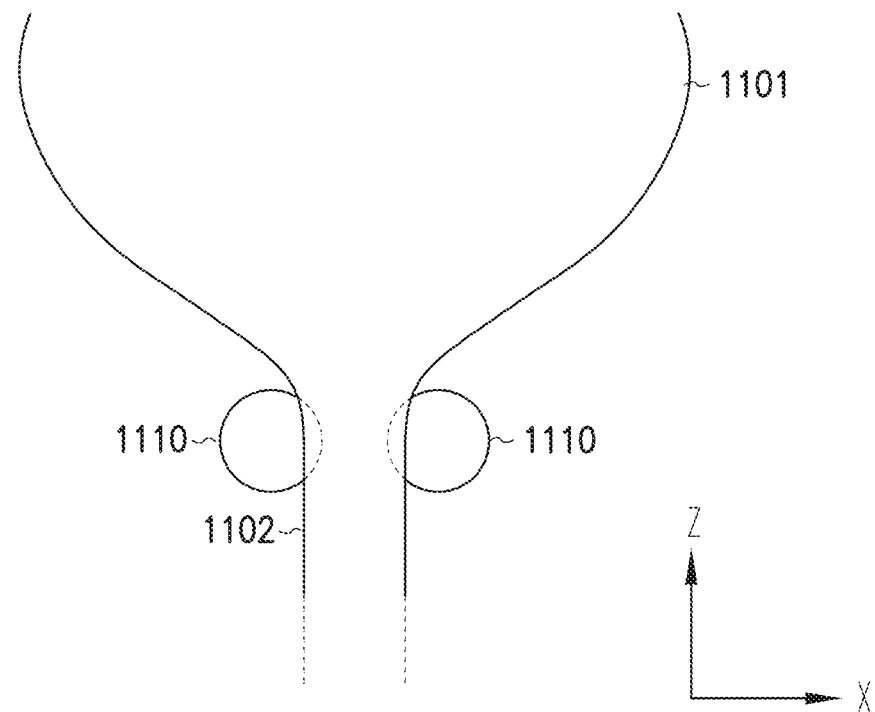
FIG. 11 is a top view showing approximate target sites of placement of implantable devices to improve coaptation of a urethra, according to an embodiment of present subject matter.

FIG. 11 is a top view of a bladder 1101 and a urethra 1102 showing approximate target sites of placement of the implantable devices 1110 to improve coaptation of a urethra, according to an embodiment of present subject matter. The implantable devices 1110 can present any embodiment of the implantable device as discussed in this document (with the expandable membrane element or the adjustable membrane element shown in the figure to illustrate its location), including but not limited to the implantable device 110, the implantable device 910, the implantable device 1010, or an implantable device including various combinations of features of the implantable devices 110, 910, and 1010. A Cartesian coordinate system with X-, Y-, and Z-axes is shown in FIGS. 11-21 (with two of the X-, Y-, and Z-axes seen in each of these figures) as a reference for exemplary orientations of structures illustrated in these figures. The orientation of the Z-axis is along the direction of the urethra 1002 in the approximate location of implantation. The location is near the bladder neck and urethral vesical anastomosis in the case of radical prostatectomy or further down the urethra at the apex of the prostate after Trans-Urethral Resection of the Prostate (TURP).

Figure 12:
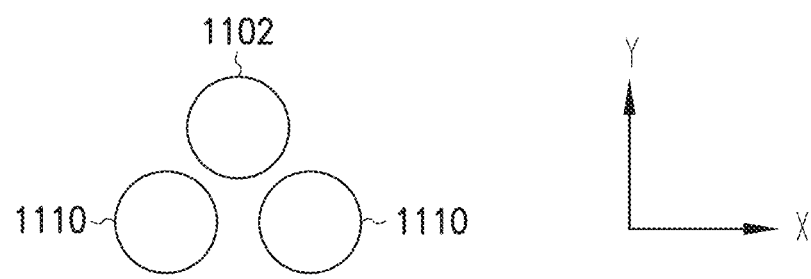
FIG. 12 is a view along the length of the urethra in the area of implantation showing approximate target sites of placement of implantable devices to improve coaptation of a urethra, according to an embodiment of present subject matter.

FIG. 12 is a view along the length of the urethra 1102 in the area of implantation (or along the y-axis) showing approximate target sites of placement of the implantable devices 1110 to improve coaptation of a urethra, according to an embodiment of present subject matter. The present subject can assist in the proper placement of the implantable devices 1110 during implantation into the patient and/or adjustment of the implantable devices 1110 after the implantation. In particular, the accurate placement of the implantable devices 1110 along the Y-axis (sagittal view) is facilitated by the applications of the present subject matter.

Figure 13:
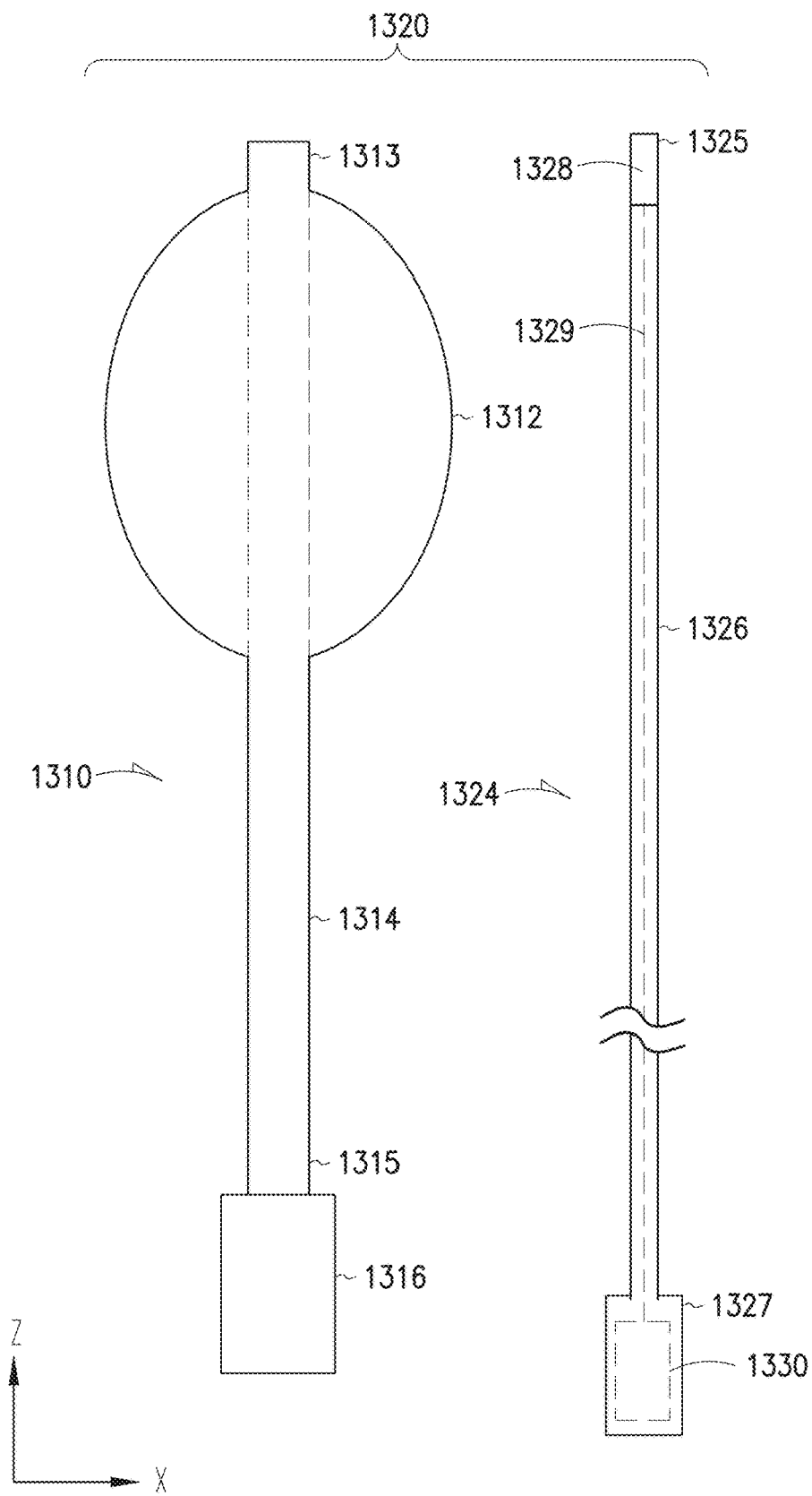
FIG. 13 is an illustration of an implantable device and a sensor probe, according to an embodiment of present subject matter.

FIG. 13 is an illustration of an implantable device kit 1320, including an implantable device 1310 and a sensor probe 1324, according to an embodiment of present subject matter. The implantable device 1310 and the sensor probe 1324 can be provided as a device kit, which may also include other accessories. The implantable device 1310 can be used to coapt a lumen in a body, and can include an adjustable membrane element 1312, an elongate the conduit 1314, and a rear port 1316. The adjustable membrane element 1312 is configured to coapt the lumen and includes a continuous wall having an inner surface defining a chamber. The conduit 1314 has a rear end 1315, a front end 1313 coupled to the adjustable membrane element 1312, a peripheral surface connected to and sealed to the adjustable membrane element 1312 near the front end 1313, and an lumen (not shown in FIG. 13) extending longitudinally in the conduit 1314 from a first opening at the rear end 1315 to a second opening at or near the front end 1313 in fluid communication with the chamber. The rear port 1316 is coupled to the rear end 1315, and includes a cavity in fluid communication with the first opening of the first lumen and an elastic septum allowing access to the cavity by a needle. In some embodiments, the rear port 1316 is releasably coupled to the rear end of the conduit 1314. The implantable devices 1310 can present any embodiment of the implantable device as discussed in this document, including but not limited to the implantable device 110, the implantable device 910, the implantable device 1010, or an implantable device including various combinations of features of the implantable devices 110, 910, and 1010.

Figures 14, 15:
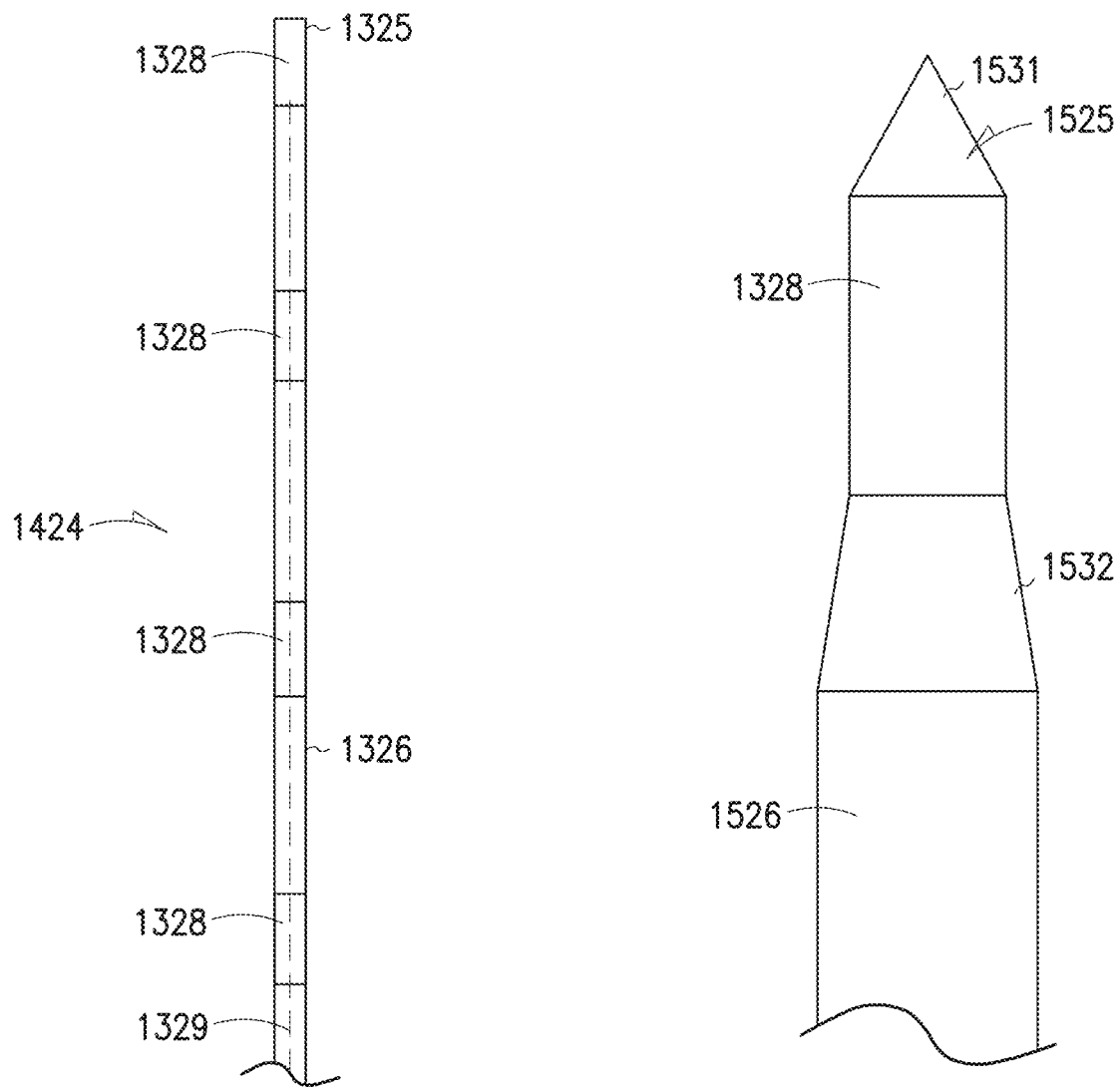
FIG. 14 is an illustration of a portion of a sensor probe, according to an embodiment of present subject matter.
FIG. 15 is an illustration of a front end of a sensor probe, according to an embodiment of present subject matter.

The sensor probe 1324 has an elongate body 1326 having a rear end 1327 a front end 1325, and one or more sensors 1328 incorporated onto the elongate body 1326. In various embodiments, the sensor probe 1324 can be constructed by incorporating the sensor(s) 1328 into any surgical tool that is used during the implantation and/or adjustment of the implantable device 1310 and has an elongate body. Examples of such a surgical tool include a push rod (e.g., push rod 1450) and a guide probe (or guide rod or guide wire, e.g., guide probe 424). In one embodiment, as illustrated in FIG. 13, one sensor 1328 at the front end 1325 is illustrated. In another embodiment, as illustrated in FIG. 14, which shows a portion of a sensor probe 1424 according to an embodiment of present subject matter, a plurality of sensors 1328 is distributed over at least a portion of the elongate body 1326.

In various embodiments, the sensor(s) 1328 can be rotated by rotating the elongate body 1326, such as by rotating the rear end 1327. The elongate body 1326 can include a sensor connection circuit 1330, such as at the rear end 1327. Conductors 1329 extend within the elongate body 1326 to provide connections between sensor(s) 1328 and sensor connection circuit 1330. In one embodiment, sensor connection circuit 1330 includes a connector for connection to an external system that processes signals sensed by sensor(s) 1328. In another embodiment, sensor connection circuit 1330 includes a telemetry circuit and a battery such that it can communicate with the external system wirelessly. The telemetry circuit can perform the wireless communication using, for example, electromagnetic, magnetic, acoustic, or optical telemetry.

In various embodiments, sensor(s) 1328 can include one or more ultrasonic transducers each to convert an electrical input signal to ultrasound, transmit the ultrasound, receive a reflected ultrasound (echo of the transmitted ultrasound), and convert the received reflected ultrasound to an electrical image signal. The external system can receive the electrical image signal and produce an ultrasonic image based on the electrical image signal. The one or more ultrasonic transducers can each include a piezoelectric transducer or a capacitive transducer, and each have an ultrasonic beam direction and an ultrasonic beam angle.

In various embodiments, sensor(s) 1328 can include one or more optical sensors. The one or more optical sensors can each include a charge-coupled device (CCD) image sensor or an active pixel sensor (APS, also known as complementary, metal-oxide-semiconductor (CMOS) image sensor) to convert captured image to an electrical image signal. The external system can receive the electrical image signal and produce a visual image based on the electrical image signal.

In various embodiments, the lumen of the implantable device 1310 that is in fluid communication with the chamber is also configured to receive the sensor probe 1324, which is used as a push rod (e.g., as illustrated in FIG. 9). The end of lumen at the front end 1313 is configured to receive a force applied through the sensor probe 1324 to move the implantable device 1310. The lumen includes a closed end near the front end 1313. The closed end has sufficient strength and hardness to receive the front end 1325 of the sensor probe 1324 and transfers force applied at the rear end 1327 of the sensor probe to the implantable device 1310.

In various other embodiments, a first lumen of the implantable device 1310 is in fluid communication with the chamber for adjusting the volume of the chamber, and the implantable device 1310 includes a second lumen extending longitudinally within at least a portion of the conduit 1314 and configured to receive the sensor probe 1324 (e.g., as illustrated in FIGS. 2, 3, 5, and 10). The second lumen includes an inlet at or near the rear end 1315 of the conduit 1314 and an outlet at or near the front end 1313 of the conduit 1314. The front end 1313 is configured to receive a force applied through the sensor probe 1324 to move the implantable device 1310.

In one embodiment, the second lumen includes a closed end near the front end 1313 of the conduit 1314. This closed end has sufficient strength and hardness to receive the front end 1325 of the sensor probe 1324 and transfers force applied at the rear end 1327 of the sensor probe 1324 to the implantable device 1310. FIG. 16 is a cross-sectional view of a portion of the front end 1613 of an elongate conduit 1614 showing a closed end of the first or second interior passage way that is configured to receive the force applied through the sensor probe 1324 to move the implantable device 1310, according to an embodiment of present subject matter. The front end 1613 can represent an example of the front end 1313. In one embodiment, the front end 1613 includes a sensor window 1635 to provide for transparency to the signals to be sensed. For example, ultrasound transparent material can be used for the sensor window 1635. The sensor window 1635 can be configured for a specified overall ultrasonic beam angle, up to 360 degrees (i.e., the sensor window has a length equal to the circumference of the second lumen).

In another embodiment, the sensor probe 1324 includes a sharp tip suitable for penetrating tissue, as in the example illustrated in FIG. 10. FIG. 15 is an illustration showing a front end 1525 of a sensor probe 1524, according to an embodiment of present subject matter. The sensor probe 1524 can represent an example of the sensor probe 1324 and includes a sharp tip 1531 at the front end 1525. The second lumen includes an outlet near the front end 1313 of the conduit 1314. The outlet allowing a portion of the sensor probe 1524 including the sharp tip 1531 to protrude from the conduit 1314. FIG. 17 is a cross-sectional view of a portion of a front end 1713 of an elongate conduit 1714, according to an embodiment of present subject matter. The front end 1713 can represent an example of the front end 1313. The second lumen includes a first shoulder 1736 and the sensor probe 1524 includes a second shoulder 1532 configured to abut the first shoulder 1736 to allow transfer of force applied at a rear end 1327 of the sensor probe 1324 to the implantable device 1310. In one embodiment, as illustrated in FIGS. 15 and 17, the first shoulder 1736 is formed by a change in diameter of the second lumen, and the second shoulder 1532 is formed by a change in diameter of the sensor probe 1524. Sensor(s) 1328 can be incorporated on to an elongate body 1526 of the sensor probe 1524 at the front end 1525 such that both the sharp tip 1531 and the sensor(s) 1328 can protrude from the conduit 1314 of implantable device 1310.

Figure 18:
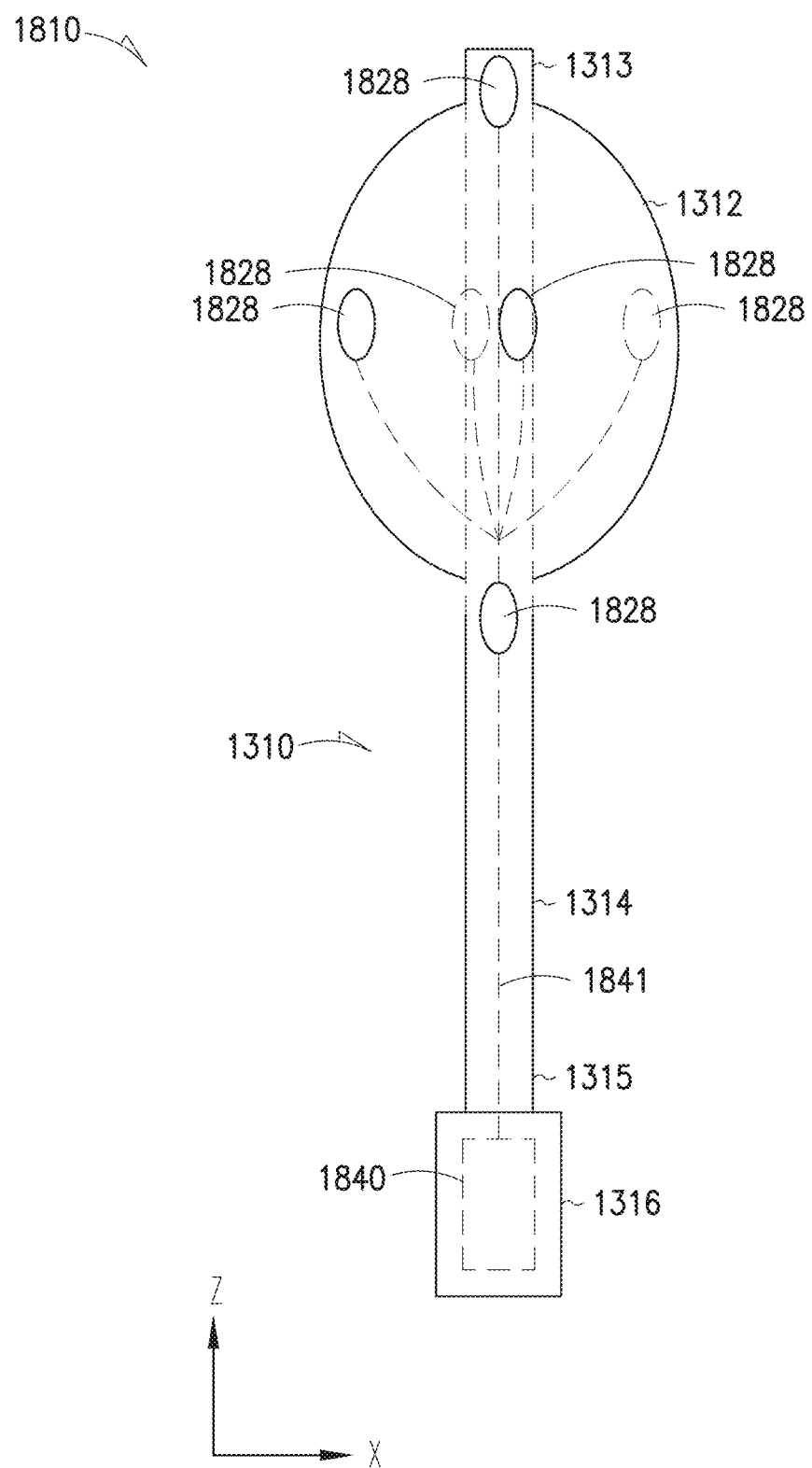
FIG. 18 is an illustration of an implantable device with one or more sensors, according to an embodiment of present subject matter.

FIG. 18 is an illustration of an implantable device 1810 with one or more sensors, according to an embodiment of present subject matter. Implantable device 1810 includes the implantable device 1310 as discussed above and one or more sensors 1828 incorporated onto the implantable device 1310. Implantable device 1810 further includes a sensor connection circuit 1840, such as at the rear end 1315, and conductors 1841 that extend within the elongate body 1314 to provide connections between sensor(s) 1828 and sensor connection circuit 1840. In the illustrated embodiment, implantable device 1810 includes six sensors 1828 at a distal connection between the adjustable membrane element 1312 and the conduit 1314, a rare connection between the adjustable membrane element 1312 and the conduit 1314, and along a midline of the adjustable membrane element 1312 that is perpendicular to the conduit (i.e., perpendicular to the Z-axis). In various embodiments, any number of sensors incorporated onto any location on the implantable device 1810. For example, one or more sensors 1828 can be incorporated onto the conduit 1314 (e.g., at or adjacent the front end 1313, at or adjacent the distal connection between the adjustable membrane element 1312 and the conduit 1314, and/or at or adjacent the rear connection between the adjustable membrane element 1312 and the conduit 1314) and/or the adjustable membrane element 1312 (e.g., on a midline of the adjustable membrane element 1312 that is perpendicular to the conduit 1314, adjacent the distal connection between the adjustable membrane element 1312 and the conduit 1314, and/or adjacent the rear connection between the adjustable membrane element 1312 and the conduit 1314.

In various embodiments, sensor(s) 1828 can include one or more ultrasonic transducers each to convert an electrical input signal to ultrasound, transmit the ultrasound, receive a reflected ultrasound (echo of the transmitted ultrasound), and convert the received reflected ultrasound to an electrical image signal. An external system can receive the electrical image signal and produce an ultrasonic image based on the electrical image signal. The one or more ultrasonic transducers can each include a piezoelectric transducer or a capacitive transducer, and each have an ultrasonic beam direction and an ultrasonic beam angle. A plurality of ultrasonic transducers can be arranged on the implantable device 1810 provide a specified overall ultrasonic beam angle (e.g., 90, 180, 270, or 360 degrees).

In various embodiments, sensor(s) 1828 can include one or more optical sensors. The one or more optical sensors can each include a CCD image sensor or an APS to convert captured image to an electrical image signal. The external system can receive the electrical image signal and produce a visual image based on the electrical image signal.

In various embodiments, sensor(s) 1828 can include one or more of any type that can sense signals useful in assisting the placement and adjustment of the implantable device 1810, such as pressure sensors and strain gauges.

The sensor connection circuit 1840 can be within the rear port 1316 and provide for access to the one or more sensors 1828 via the rear port 1316. In one embodiment, the implantable deice 1810 can communicate with the external system using a wired connection. The sensor connection circuit 1840 includes a connector. The external system includes a percutaneous connector to pierce the elastic septum of the rear port 1316 and mate the connector in the rear port 1316, In another embodiment, the implantable deice 1810 can communicate with the external system wirelessly. The sensor connection circuit 1840 includes a telemetry circuit and a battery or inductive power receiver. The telemetry circuit can transmit power to the implantable device 1810 and receive the sensed signals from the implantable device 1810.

Figure 19:
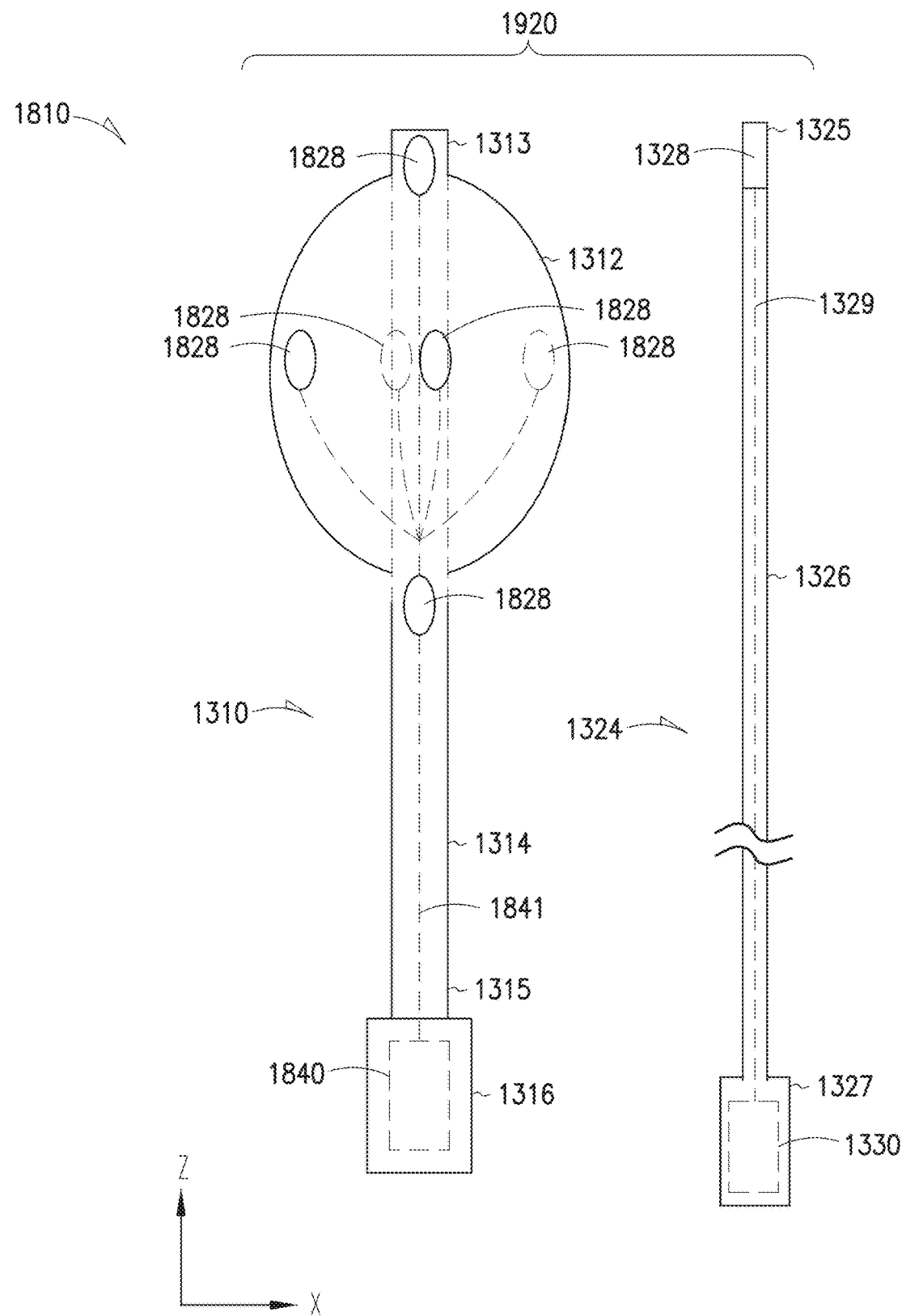
FIG. 19 is an illustration of an implantable device kit, according to an embodiment of present subject matter.

FIG. 19 is an illustration of an implantable device kit 1920, according to an embodiment of present subject matter. Implantable device kit includes at least an implantable device 1810 and a sensor probe 1324, as illustrated in FIG. 19, and can also include other tools or accessories used for implantation of the implantable device 1810. One or more sensors selected from sensor(s) 1828 and sensor(s) 1328 can be used to provide for monitoring of the implantable device 1810 during implantation and/or adjustment. For various purposes and circumstances, a user can use one or more sensors of implantable device 1810 only, one or more sensors of sensor probe 1324 only, or sensors of both implantable device 1810 and sensor probe 1324 for the monitoring.

Figure 20:
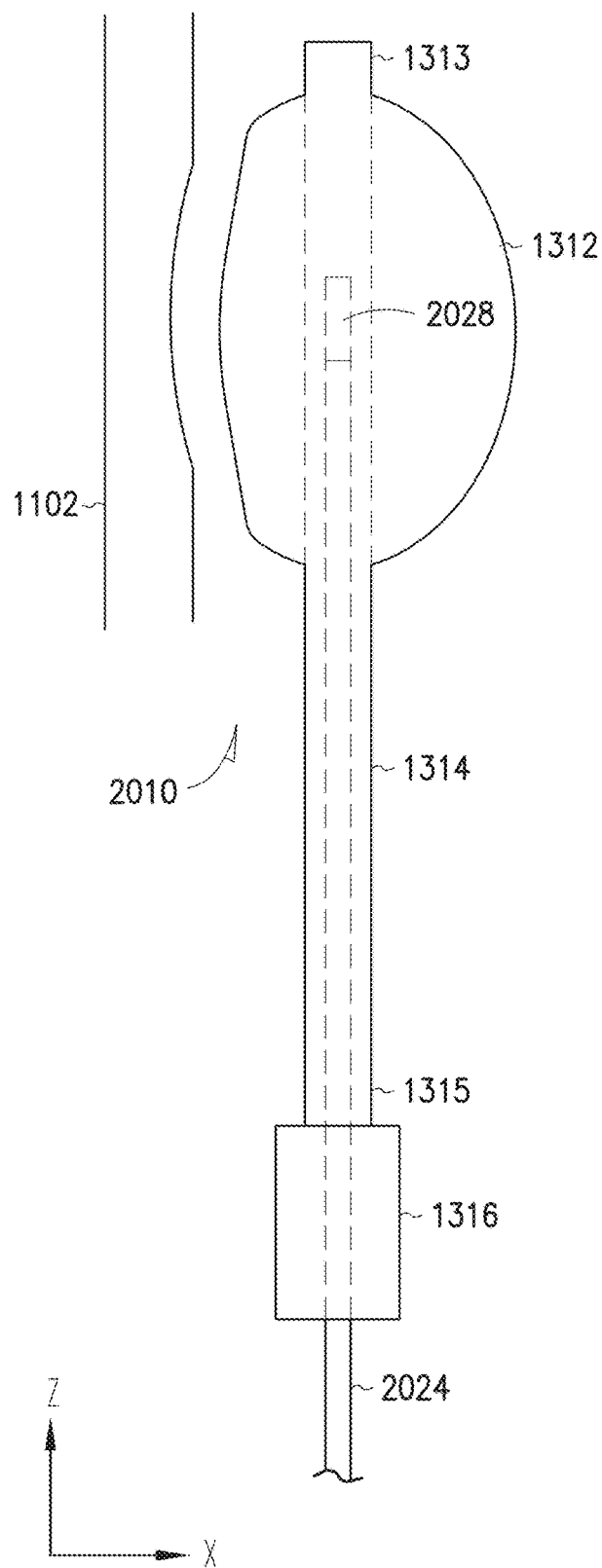
FIG. 20 is an illustration of coaptation of a body lumen using an implantable device, according to an embodiment of present subject matter.

FIG. 20 is an illustration of coaptation of the body lumen 1102 using an implantable device 2010 and a probe 2024, according to an embodiment of present subject matter. Examples of implantable device 2010 include, but are not limited to, any implantable device (with or without the one or more sensors) discussed in this document, such as implantable devices 110, 910, 1010, 1310 and 1810. Examples of the probe 2024 include, but are not limited to, any probes (with or without the one or more sensors) discussed in this document, such as the guide probe 424, the push rod 1450, and the sensor probes 1324, 1424, and 1524, A sensor 2028 represents any one or more sensors that are incorporated onto implantable device 2010 and/or probe 2024. In one embodiment, sensor 2028 provides an image such as the one shown in FIG. 22 for guiding the placement of the implantable device 2010 adjacent the lumen 1102 (e.g., the urethra) for coaptation of the lumen, and/or allows for determination of whether the body lumen is coapted to a desirable extent.

Figure 21:
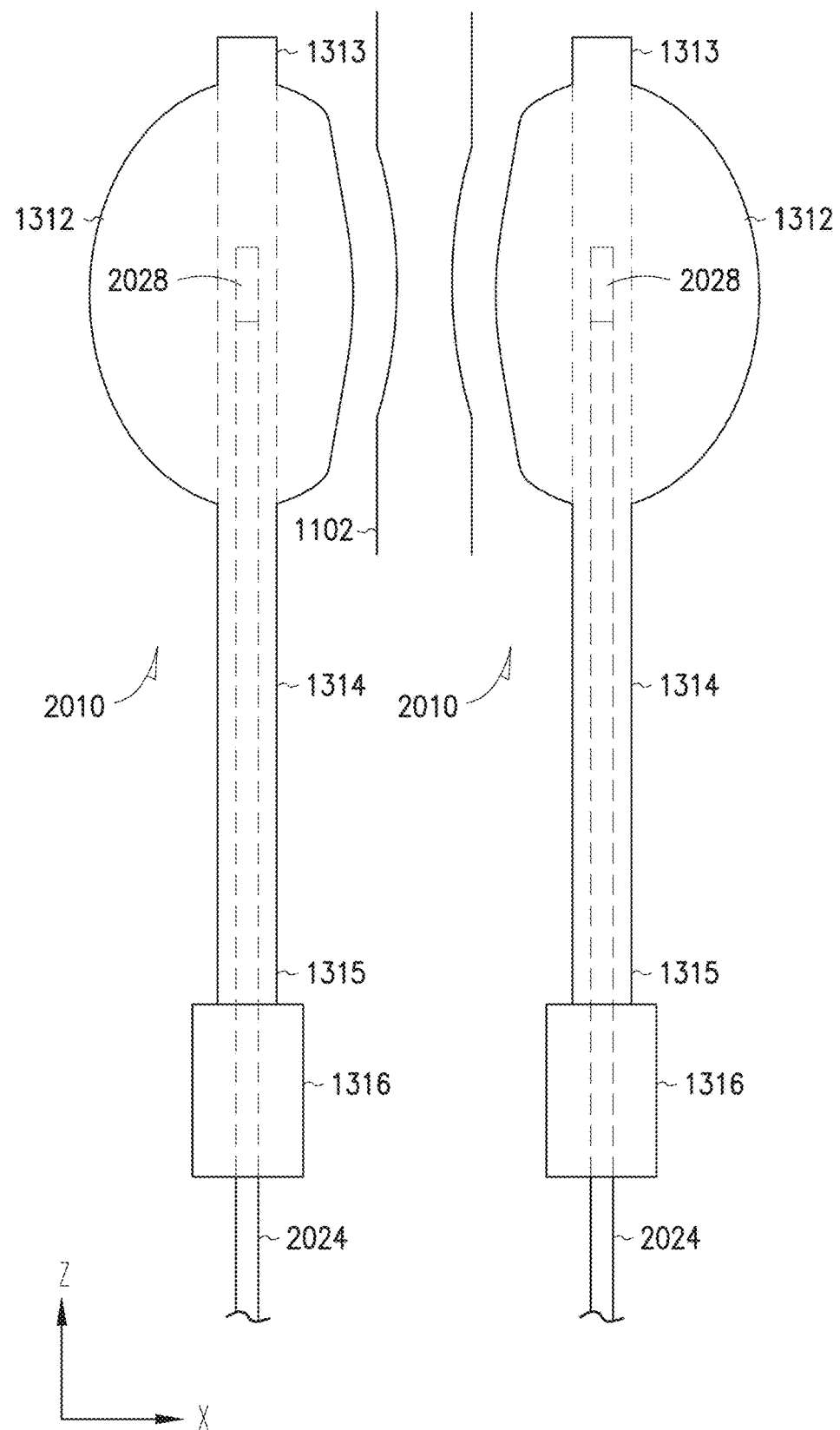
FIG. 21 is an illustration of coaptation of a body lumen using two implantable devices, according to an embodiment of present subject matter.
Figure 22:
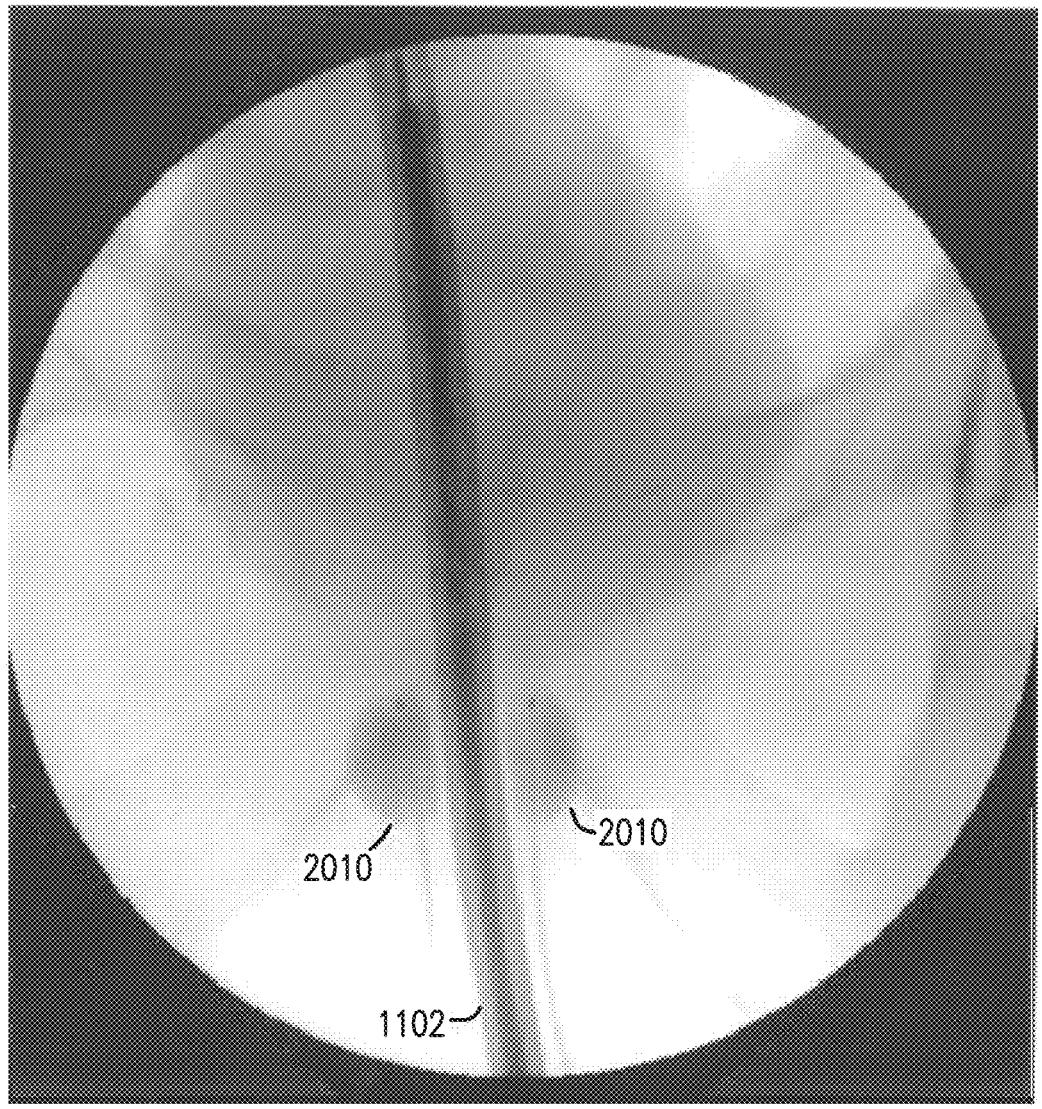
FIG. 22 is an image showing two implantable devices implanted in a patient adjacent to a body lumen for coaptation of that body lumen, according to an embodiment of present subject matter.
Figure 23:
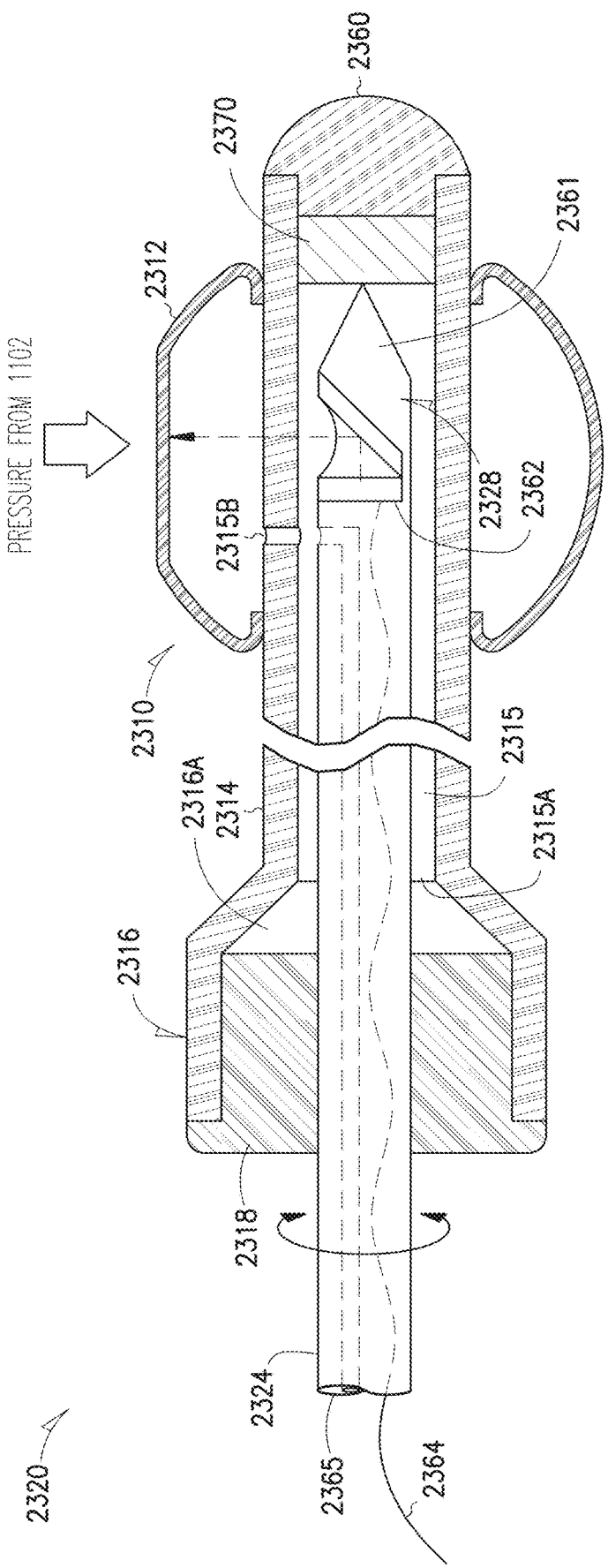
FIG. 23 is an illustration of a single-lumen implantable device and a sensor probe, according to an embodiment of present subject matter.

FIG. 21 is an illustration of coaptation of the body lumen 1102 using two implantable devices 2010 and two probes 2024, according to an embodiment of present subject matter. FIG. 22 shows an example of an image of this therapy. When the body lumen (e.g., the urethra) is properly coapted, flattening of the adjustable membrane elements 1312 of each implantable device facing the lumen is observed. In various embodiments, sensors 2028 can be used to provide images and/or other information indicative of the position of each of the implantable devices 2010, the degree of flattening of the adjustable membrane elements 1312, and/or the shape of the body lumen, thereby providing for guidance in placing and/or adjusting the implantable devices 2010, The shape of the body lumen can indicate a degree of the coaptation of the body lumen. In various embodiments, sensor 2028 placed in each of the implantable device 2010 can detect information indicative of a shape of the adjustable membrane element 1312 of the same implantable device, a position of the adjustable membrane element 1312 of the same implantable device (e.g., relative to the body lumen 1102), a shape of the adjustable membrane element 1312 of the other implantable device 2010, a position of the adjustable membrane element 1312 of the other implantable device 2010 (e.g., relative to the body lumen 1102), and/or a shape of the body lumen 1102. In various embodiments, sensor 2028 placed in the implantable device 2010 can detect information indicative of a shape and/or a position of another implantable device, or a portion thereof, that is present in the tissue near the implantable device 2010, FIG. 23 is an illustration of an implantable device kit 2320, including a single-lumen implantable device 2310 and a sensor probe 2324, according to an embodiment of present subject matter. The implantable device kit 2320 can represent an example of implantable device kit 1320, with the implantable device 2310 used for coaptation of a urethra and the sensor probe 2324 used for detecting one or more indications of a state or degree of the coaptation of the urethra and adjusting the volume in an adjustable membrane element 2312 of implantable device 2310 for optimal efficacy in treating urinary incontinence without creating obstruction of the urethra. The implantable device 2310 includes a front end 2360, a rear port 2316, and an elongate conduit 2314 connected between the front end 2360 and the rear port 2316. The adjustable membrane element 2312 is affixed onto the conduit 2314 near the front end 2360 and includes a continuous wall having an inner surface defining a chamber. A lumen 2315 extends longitudinally within the conduit 2314 and is in fluid communication with the chamber of the adjustable membrane element 2312 at a distal opening 2315B and with a cavity 2316A of the rear port 2316 at rear opening 2315A. In the illustrated embodiment, the sensor probe 2324 is a 3-in-1 device that can also be used as (1) a sensing device including a sensor 2328 at a front end of the sensor probe 2324, (2) a push rod to advance the implantable device 2310 in tissue by applying force against a closed front end of the lumen 2315 at the front end 2360, and (3) an hallow needle that includes a lumen 2365 through which a fluid can be introduced and withdrawn for inflating and deflating the adjustable membrane element 2312, respectively, through the distal opening 2315B of the lumen 2315. The lumen 2315 is configured to accommodate the front portion of the sensor probe 2324 with the front end of the sensor probe 2324 reach the closed front end of the lumen 2315. As shown in FIG. 23, pressure from the urethra may flatten a side of the adjustable membrane element 2312 when the adjustable membrane element 2312 is placed adjacent the urethra and inflated. The sensor 2328 can allow for observation of such flattening, which indicates the amount of pressure that can be adjusted for the optical efficacy of treating the urinary incontinence.

As shown in FIG. 23, the adjustable membrane element 2312 is inflated to provide urethral coaptation and has a flattened portion where it meets resistance to expansion from the urethra. The implantable device 2310 includes a radiopaque marker 2370 at the front end 2360. The radiopaque marker 2370 also serves as a stop for the sensing probe 2324 to assure that it is in the right position for sensing. The stop also serves as a stop for a push rod (e.g., the sensor probe 2324 used as the push rod) for placement of the implantable device 2310 in an initial implantation procedure. When the sensor probe 2324 is used as the push rod, the placement and/or initial adjustment of the implantable device 2310 can be guided using the sensor 2328 to observe the coaptation of the urethra. The rear port 2316 includes a self-sealing septum 2318 to allow access to the lumen 2315 by the sensor probe 2324 (as well as other push rod or push-wire, if used). The front end of the sensor probe 2324 has a sharp tip for piercing through the septum 2318. The advantage of a single lumen implantable device includes providing more cross-sectional area to accommodate the sensor 2328 in the conduit 2314 of a given diameter.

In the illustrated embodiment, the sensor 2328 is an optical sensor for visually observing the flattening of the adjustable membrane element 2312 against the urethra as a proxy for actual visualization of coaptation within the urethra. In another embodiment, the sensor 2328 is an ultrasonic sensor. In addition to directly observing the coaptation of the urethra, if the ultrasonic sensor transmits an ultrasound having sufficient depth of penetration within the tissue, it may also allow for visualization of the adjustable membrane element 2312 in relation to anatomic structures such as the bladder neck and the rectum. Such visualization can be used to aid placement of the adjustable membrane element 2312 during the implantation of the implantable device 2310. In various embodiments, the sensor 2328 can include any type of sensor that allows for detection of the flattening of the adjustable membrane element 2312 and/or visualization of the adjustable membrane element 2312 in the tissue in relation to various anatomic structures.

In the illustrated embodiment, the sensor 2328 (i.e., the optical sensor) includes an optical sensing element 2361 for observing the flattening of the adjustable membrane element 2312 with a CCD or CMOS chip 2362 that obtains a radial view with the aid of a mirror 2363. The chip 2362 is powered, and data acquired by the sensor 2328 are returned, via filament 2364. The filament 2364 can also be used to power a light source such as an LED to aid in visualization (which is unnecessary if the chip 2362 is an infrared CCD or CMOS chip). The sensor probe 2324 can be rotated about its longitudinal axis within the lumen 2315 to scan circumferentially to find the point of maximum coaptation where the adjustable membrane element 2312 is flattened. Rotating the sensor probe 2324 can also aid in passing it through curves in the conduit 2314, especial when the rear port 2316 is routed into the scrotum or labia. At least for this reason, the sensor probe 2324 is provided with a certain amount of flexibility. In one embodiment, the sensor probe 2324 with the optical sensor 2328 is equipped with a wide-angle lens to allow for viewing the entire internal surface of the adjustable membrane element 2312 such that circumferential scanning would not be necessary.

In another embodiment, the sensor probe 2324 can include a borescope for optical visualization with a fiber optic bundle extending through the sensor probe. A light source within the sensor probe 2324 is unnecessary because the fibers can also be used to transmit light from a light source externally connected to the sensor probe. The fiber optic bundle may have a diameter that is substantially smaller when compared to the size of a CCD or CMOS chip, thereby reducing the diameter of the sensor probe 2324 and hence the diameter of the conduit 2314 and rear port 2316. This allows for a reduction of the overall size of the implantable device 2310 and the overall size of the sensor probe 2328. A smaller diameter for the sensor probe 2324 is desirable because it has to pass through the skin of the scrotum or labia to reach the rear port 2316 of the implantable device 2310 after it is implanted in the patient. Additionally, the fiber optic implementation of the sensor probe 2324 may reduce the cost of production when compared to the optical sensor implementation with CCD or CMOS chip, thereby improving affordability of making the sensor probe 2324 as a disposable device.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An implantable device kit for controllable coaptation of a body lumen in tissue of a living body, comprising:
    two implantable devices each including:
        an adjustable membrane element including a continuous wall having an inner surface defining a chamber, the adjustable membrane element configured to coapt the body lumen;
        an elongate conduit including a conduit peripheral surface, a conduit rear end, a conduit front end, and a conduit lumen, the conduit peripheral surface connected to and sealed to the adjustable membrane element at or near the conduit front end, the conduit lumen having a first opening at the conduit rear end, a second opening in fluid communication with the chamber; and a closed end at or near the conduit front end; and
        a rear port connected to the conduit rear end and including a cavity in fluid communication with the first opening of the conduit lumen; and
    two sensor probes each configured to be partially placed in one implantable device of the two implantable devices and each including:
        a probe front end having a sharp tip and configured to enter the conduit lumen of the one implantable device by piercing through the rear port of the one implantable device and reach the closed end of the conduit lumen; and
        a sensor configured to detect information indicative of a degree of the coaptation of the body lumen,
    wherein the two implantable devices are each configured to be completely enclosed within the tissue by implantation with the adjustable membrane element adjacent the body lumen.

2. The implantable device kit of claim 1, wherein the two sensor probes each comprise a probe lumen configured to be in fluid communication with the chamber of the adjustable membrane element of the one implantable device when the probe front end is within the conduit lumen of the one implantable device at the closed end of the conduit lumen, to allow for inflation of the adjustable membrane element by introducing a fluid into the chamber through the probe lumen, and to allow for deflation of the adjustable membrane element by withdrawing the fluid from the chamber through the probe lumen.

3. The implantable device kit of claim 2, wherein the two sensor probes are each configured for use as a push rod for advancing the one implantable device in the tissue during an implantation of the one implantable device.

4. The implantable device kit of claim 3, wherein the sensor comprises an optical sensor.

5. The implantable device kit of claim 4, wherein the optical sensor comprises a camera.

6. The implantable device kit of claim 4, wherein the optical sensor comprises a fiber optic borescope.

7. The implantable device kit of claim 1, wherein the sensor comprises an ultrasonic sensor.

8. The implantable device kit of claim 1, wherein the conduit front end comprises a sensor window providing for transparency to a signal to be received by the sensor when the sensor is placed in the conduit lumen.

9. An implantable device kit for controllable coaptation of a body lumen in tissue of a living body, comprising:
    two sensor probes each including a probe front end and a sensor incorporated onto the probe front end and configured to detect information indicative of a degree of the coaptation of the body lumen; and
    two implantable devices each including:
        an adjustable membrane element including a continuous wall having an inner surface defining a chamber, the adjustable membrane element configured to coapt the body lumen;
        an elongate conduit including a conduit peripheral surface, a conduit rear end, a conduit front end, a first conduit lumen, and a second conduit lumen, the conduit peripheral surface connected to and sealed to the adjustable membrane element at or near the conduit front end, the first conduit lumen having a first opening at the conduit rear end and a second opening in fluid communication with the chamber, the second conduit lumen having an inlet configured to receive a portion of the sensor probe including the probe front end and an closed end at or near the conduit front end and is configured to allow the probe front to advance to the closed end; and
        a rear port connected to the conduit rear end and including a cavity in fluid communication with the first opening of the first conduit,
    wherein the two implantable devices are each configured to be completely enclosed within the tissue by implantation with the adjustable membrane element adjacent the body lumen.

10. The implantable device kit of claim 9, wherein the two sensor probes are each configured for use as a push rod for advancing one implantable device in the tissue during an implantation of that implantable device.

11. The implantable device kit of claim 9, wherein the sensor comprises an optical sensor.

12. The implantable device kit of claim 11, wherein the optical sensor comprises a camera.

13. The implantable device kit of claim 11, wherein the optical sensor comprises a fiber optic borescope.

14. The implantable device kit of claim 9, wherein the sensor comprises an ultrasonic sensor.

15. The implantable device kit of claim 9, wherein the conduit front end comprises a sensor window providing for transparency to a signal to be received by the sensor when the sensor is placed in the second conduit lumen.

16. The implantable device kit of claim 9, wherein the second conduit lumen comprises an outlet at or near the conduit front end allowing the probe front end including the sensor to protrude from the elongate conduit.

17. A method for controllable coaptation of a body lumen in tissue of a living body, comprising:
    providing controllable coaptation of the body lumen using two implantable devices each including:
        an adjustable membrane element including a continuous wall having an inner surface defining a chamber; and
        an elongate conduit including a conduit peripheral surface connected to and sealed to the adjustable membrane element, a conduit rear end, a conduit front end, and a conduit lumen extending longitudinally in the conduit from a first opening at the rear end to a second opening in fluid communication with the chamber of the implantable device for adjustably expanding or contracting the adjustable membrane element by a flowable material introduced through the first opening, wherein the two implantable devices are each configured to be completely enclosed within the tissue by implantation with the adjustable membrane element adjacent the body lumen; and providing two sensor probes each configured to be partially placed in one implantable device of the two implantable devices and including a sensor configured to detect information indicative of a degree of the coaptation of the body lumen when the sensor probe is partially placed in the one implantable device after the one implantable device is completely enclosed within the tissue.

18. The method of claim 17, wherein providing the two sensor probes comprises providing two sensor probes each including a portion configured to be placed in the conduit lumen with the sensor positioned in the conduit lumen at or near the conduit front end.

19. The method of claim 17, further comprising providing each device of the two implantable devices with an additional conduit lumen extending longitudinally in the conduit from an inlet configured to receive a portion of one probe of the two sensor probes to a front end at or near the conduit front end.

20. The method of claim 17, further comprising detecting at least one of a shape of the adjustable membrane element or a position of the adjustable membrane element of each implantable device of the two implantable devices when at least one sensor probe of the two sensor probes is partially placed in one implantable device of the two implantable devices.

* * * * *